US006255515B1

(12) United States Patent
Kato et al.

(10) Patent No.: US 6,255,515 B1
(45) Date of Patent: Jul. 3, 2001

(54) PROCESSES FOR PRODUCING SILICON- OR GERMANIUM-CONTAINING ORGANIC COMPOUND, TRANSITION METAL COMPLEX, CATALYST FOR POLYMERIZATION OF α-OLEFIN AND α-OLEFIN POLYMER

(75) Inventors: Taku Kato, Yokohama; Kazuya Okano, Inashiki-gun; Toshihiko Sugano, Yokkaichi; Yutaka Ohtani, Kobe; Hirohisa Kitagawa, Nagaokakyo; Sugio Nishimura, Yokohama, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/341,844

(22) PCT Filed: Jan. 20, 1998

(86) PCT No.: PCT/JP98/00201

§ 371 Date: Aug. 31, 1999

§ 102(e) Date: Aug. 31, 1999

(87) PCT Pub. No.: WO98/31690

PCT Pub. Date: Jul. 23, 1998

(30) Foreign Application Priority Data

Jan. 21, 1997 (JP) .................................................... 9-23204

(51) Int. Cl.[7] ........................................................ C07F 7/08
(52) U.S. Cl. ............................ 556/478; 556/87; 556/95; 556/96; 556/480

(58) Field of Search .................................... 556/478, 480, 556/87, 95, 96

(56) References Cited

U.S. PATENT DOCUMENTS 5,103,030   4/1992   Rohrmann et al. .

FOREIGN PATENT DOCUMENTS

| 2119540 | 9/1994 | (CA) . |
| 0320762A2 | 6/1989 | (EP) . |
| 6-271594 | 9/1994 | (JP) . |
| 617044 A2 | 9/1994 | (EP) . |
| 8-337587 | 12/1996 | (JP) . |

OTHER PUBLICATIONS

Chu et al J. Organometallic Chemistry, 271 (1984) 327–336 Tertiary Alcoholysis of Chlorosilanes via etc.
Lennon et al Organometallics 1989, 8, 1121–1122 Nucleophilic Catalysis of Organosilicon etc.

*Primary Examiner*—Paul F. Shaver
(74) *Attorney, Agent, or Firm*—Nixon & Vnaderhye

(57) ABSTRACT

An alkali metal- or alkali earth metal-containing organic compound (i) is reacted with a leaving group- and silicon- or germanium-containing compound (ii) in the presence of a nitrogen-containing aromatic heterocyclic compound. By such a method, it is possible to produce a silicon- or germanium-containing organic compound, for example, a cyclopentadienyl compound cross-linked by a silicon atom or a germanium atom, typically a cyclopentadienyl compound which is substituted with a substituted or unsubstituted silyl or germyl group, for a short time with a high yield.

10 Claims, No Drawings

PROCESSES FOR PRODUCING SILICON- OR GERMANIUM-CONTAINING ORGANIC COMPOUND, TRANSITION METAL COMPLEX, CATALYST FOR POLYMERIZATION OF α-OLEFIN AND α-OLEFIN POLYMER

TECHNICAL FIELD

The present invention relates to processes for producing a silicon- or germanium-containing organic compound, a transition metal complex, an catalyst for polymerization of α-olefin and an α-olefin polymer, and more particularly, to improved processes for producing the above-mentioned compounds for a short time with a high yield. In accordance with the present invention, a cyclopentadienyl compound having a substituted or unsubstituted silyl or germyl group, can be produced for a short time with a high yield, for example, by substituting a hydrogen atom of a cyclopentadienyl group with silicon or germanium.

BACKGROUND ART

Metallocene catalysts which are known as homogeneous catalysts for the polymerization of α-olefin, can show a high polymerization activity and are capable of producing a polymer with a narrow molecular weight distribution. In particular, when using a stereorigid transition metal complex containing a ligand having such a structure that two cyclopentadienyl groups are cross-linked with each other, it is possible to obtain isotactic polypropylene (e.g., refer to "Journal of American Chemical Society", Vol. 106, p. 6355, etc.).

Further, it is also known to obtain polypropylene having a high isotacticity by using a transition metal complex having such a structure that two cyclopentadienyl groups are cross-linked with each other by a silicon atom (e.g., refer to Japanese Patent Application Laid-Open (KOKAI) Nos. 63-295607 -and 1-275609, etc.).

In addition, in order to enhance the isotacticity and molecular weight of polypropylene, it is known to use compounds having an indenyl group as a part of a ligand thereof into which a substituent group is introduced (e.g., refer to Japanese Patent Application Laid-Open (KOKAI) Nos. 4-268307 and 6-157661, etc.).

On the other hand, for example, from Japanese Patent Application Laid-Open (KOKAI) No. 2-76887, it is also known to obtain isotactic polypropylene by using a transition metal complex having such a structure in which two cyclopentadienyl groups are cross-linked with each other by a silicon atom or a germanium atom.

The above-mentioned cyclopentadienyl compounds as a ligand of the transition metal complex which are cross-linked by a silicon atom or a germanium atom, can be usually produced by reacting (i) an alkali metal salt or an alkali earth metal salt of a cyclopentadienyl compound with (ii) a halogenated silicon compound or a halogenated germanium compound.

For instance, Jutzi et al. have reported that upon producing dimethyl bis(tetramethylcyclopentadienyl) silane, tetramethylcyclopentadienyl lithium and dichlorodimethyl silane are heat-refluxed in tetrahydrofuran (THF) as a solvent for 5 days, and that the yield is 65% (refer to "Chemische Berichte", vol. 119, p. 1750).

In addition, Winter et al. have reported that upon producing dimethyl bis(2-methyl indenyl) silane, a lithium salt of 2-methyl indene was dropped into a diethyl ether solution of dichlorodimethyl silane for 5 hours and then stirred overnight at room temperature, and further allowed to stand for a weekend period, and that the yield was 16% (refer to Japanese Patent Application Laid-Open (KOKAI) No. 4-268307).

On the other hand, there is also known such improved techniques for efficiently producing two cyclopentadienyl compounds which are cross-linked with each other by a silicon atom or a germanium atom. For instance, in Japanese Patent Application Laid-Open (KOKAI) No. 7-252287, it has been taught that in order to enhance the yield of a compound having two cyclopentadienyl groups cross-linked with each other by a silicon atom, a substituted cyclopentadiene is reacted with dimethyl dihalosilane under the coexistence of a metal salt-type base and a metal ion-capturing agent. As such metal ion-capturing agents, there are known, for example, N,N,N',N'-tetramethyl ethylene diamine or the like (Japanese Patent Application Laid-Open (KOKAI) No. 6-279477).

Further, in Japanese Patent Application Laid-Open (KOKAI) No. 6-271594, it has been described that a lithium salt, a sodium salt or a potassium salt of a cyclopentadienyl compound is reacted with a halogenated silicon compound or a halogenated germanium compound in the presence of a cyanide or a thiocyanate, thereby enhancing the yield.

In order to obtain the above cyclopentadienyl compounds which are cross-linked by a silicon atom or a germanium atom, it is necessary to conduct the reaction for a long period of time as described above. In addition, the yield is not necessarily satisfactory. In particular, in the case where two or more sterically bulky substituent groups are bonded to the silicon atom or the germanium atom, the above disadvantageous tendency becomes more remarkable, thereby further deteriorating the yield.

In general, production processes showing a poor yield require large costs for purifying the reaction products, resulting in economical disadvantages. In addition, in the case where the metallocene compound is produced from a low-purity compound as a raw material, the purity of the obtained metallocene compound also becomes low, and the purification of the compound also requires large costs.

As described above, the conventional techniques for improving the yield of the cyclopentadienyl compound cross-linked by a silicon atom or a germanium atom, are still unsatisfactory in effects thereof, and further require the use of harmful compounds such as cyanides which tend to exhibit a toxicity to human bodies, etc. Accordingly, if such a production process capable of producing the cyclopentadienyl compound cross-linked by a silicon atom or a germanium atom with a high yield, could be established by using harmless compounds, the process is industrially advantageous.

DISCLOSURE OF THE INVENTION

The present invention has been made to solve the above-mentioned problems or disadvantages. It is an object of the present invention to provide a process for producing a silicon- or germanium-containing organic compound, for example, a cyclopentadienyl compound cross-linked by a silicon atom or a germanium atom, more typically a cyclopentadienyl compound which is substituted with a substituted or unsubstituted silyl or germyl group, for a short time with a high yield without using such compounds which tend to exhibit any toxicity to human bodies or the like. In addition, it is another object of the present invention to provide processes for producing a transition metal complex, a catalyst for the polymerization of α-olefin, and an α-olefin polymer, respectively, using the above compound.

As a result of the prevent inventors' earnest studies, it has been found that by conducting the reaction in the presence of a specific compound, the above cyclopentadienyl compound can be produced for a short time with a high yield. The present invention has been attained on the basis of the finding.

That is, in the first aspect of the present invention, there is provided a process for producing a silicon- or germanium-containing organic compound (iv) which process comprises reacting an alkali metal- or alkali earth metal-containing organic compound (i) with a leaving group- and silicon- or germanium-containing compound (ii) in the presence of a nitrogen-containing aromatic heterocyclic compound (iii).

In the second aspect of the present invention, there is provided a process for producing a transition metal complex which process comprises reacting the silicon- or germanium-containing organic compound (iv) obtained by the above process with a transition metal compound.

In the third aspect of the present invention, there is provided a process for producing a catalyst for the polymerization of α-olefin using the transition metal complex obtained by the above process.

In the fourth aspect of the present invention, there is provided a process for producing an α-olefin polymer using the catalyst obtained by the above process.

The present invention will be described in detail below. First, the process for producing the silicon- or germanium-containing organic compound according to the present invention, will be explained. In the present invention, as starting materials to be reacted, there are used an alkali metal- or alkali earth metal-containing organic compound (i) (hereinafter referred to merely as "organic metal salt") and a leaving group- and silicon- or germanium-containing compound (ii) (hereinafter referred to merely as "silicon (germanium) compound").

As the above-mentioned organic metal salts (i), there may be preferably used such compounds represented by the general formula (I), (II) or (III):

A-M$^1$           (I)

A-M$^2$-A         (II)

A-M$^2$-X         (III)

wherein $M^1$ is an alkali metal; $M^2$ is an alkali earth metal; A is a cyclopentadienyl group which may have a condensed ring, an alkyl group, an aryl group, an allyl group, a vinyl group or a heterocyclic group; and X is a halogen atom. The above-mentioned respective groups may have substituent(s), and the two As of the general formula (II) may be different from each other.

As the preferred alkali metals or alkali earth metals capable of forming the organic metal salts, there may be exemplified lithium, sodium, potassium or magnesium, though not particularly limited thereto.

In the present invention, as substituents which may be bonded to a cyclopentadienyl group constituting a metal salt of cyclopentadienyl group used as the organic metal salt (i) (hereinafter referred to as merely "a metal salt of cyclopentadienyl compound"), there may be exemplified a $C_1$ to $C_{20}$ alkyl group, a $C_3$ to $C_{20}$ cycloalkyl group, a $C_2$ to $C_{20}$ alkenyl group, a $C_2$ to $C_{20}$ alkynyl group, a $C_6$ to $C_{20}$ aryl group, a $C_7$ to $C_{20}$ arylalkyl group, a $C_1$ to $C_{20}$ alkoxy group, a $C_3$ to $C_{20}$ cycloalkoxy group, a $C_6$ to $C_{20}$ aryloxy group, an amino group which may be monosubstituted or disubstituted with $C_1$ to $C_{20}$ alkyl-, an urea group which may be monosubstituted or disubstituted with $C_1$ to $C_{20}$ alkyl, a $C_1$ to $C_{20}$ haloalkyl group, a $C_6$ to $C_{20}$ haloaryl group, a $C_1$ to $C_{20}$ haloalkoxy group, a silyl group containing a $C_1$ to $C_{20}$ hydrocarbon group, a stannyl group containing a $C_1$ to $C_{20}$ hydrocarbon group, or the like. In addition, the oxygen atom of these substituents may be further substituted with a sulfur atom. Further, there may be also exemplified a nitro group, a halogen atom or the like. As to the number of these substituents, either a single substituent or a plurality of substituents may be bonded to the cyclopentadienyl group. In the case where a plurality of the substituents are bonded, these substituents may be the same or different.

Specific examples of the above alkyl groups may include methyl, ethyl, n-propyl, i-propyl, n-butyl, sec-butyl, tert-butyl, pentyl, hexyl or the like. Specific examples of the above cycloalkyl groups may include cyclopropyl, cyclobutyl, cyclopentyl, cyclohexyl or the like. Specific examples of the above alkenyl groups may include vinyl, allyl, 2-butenyl or the like.

Specific examples of the above alkynyl groups may include ethynyl, 2-propynyl or the like. Specific examples of the above aryl groups may include phenyl, naphthyl, phenanthryl, anthryl or the like. Specific examples of the above arylalkyl groups may include benzyl or the like. Specific examples of the above alkoxy groups may include methoxy, ethoxy, butoxy or the like. Specific examples of the above cycloalkoxy groups may include cyclopropoxy or the like.

Specific examples of the above aryloxy groups may include phenoxy or the like. Specific examples of the above amino groups may include, in addition to amino, methylamino, dimethylamino, diethylamino or the like. Specific examples of the above urea groups may include, in addition to an urea group, an N',N'-dimethyl urea group, an N,N',N'-trimethyl urea group or the like. Specific examples of the above haloalkyl groups may include fluoromethyl, difluoromethyl, trifluoromethyl, pentafluoroethyl or the like.

Specific examples of the above haloaryl groups may include o-fluorophenyl, m-fluorophenyl, p-fluorophenyl, o-chlorophenyl, m-chlorophenyl, p-chlorophenyl, 2,3-difluorophenyl, 2,4-difluorophenyl, 2,5-difluorophenyl, 2,6-difluorophenyl, 2,4,6-trifluorophenyl, pentafluorophenyl or the like.

Specific examples of the above haloalkoxy groups may include fluoromethoxy, difluoromethoxy, trifluoromethoxy, pentafluoroethyoxy or the like. Specific examples of the above silyl groups may include trimethylsilyl, triethylsilyl, tributylsilyl, diphenylmethylsilyl, dimethylphenylsilyl or the like. Specific examples of the above stannyl groups may include trimethylstannyl, triethylstannyl, tributylstannyl, diphenylmethylstannyl, dimethylphenylstannyl or the like. Specific examples of the above halogen atoms may include fluorine, chlorine, bromine or iodine.

The above-mentioned substituents may form a ring together with two adjacent carbon atoms on the cyclopentadienyl group. As compounds forming such a ring, there may be exemplified indene compounds, 4,5,6,7-tetrahydroindene compounds, fluorene compounds, dihydroazulene compounds, hexahydroazulene compounds or the like.

The above substituents may be further substituted with, in addition to the same kinds of substituents described above, other substituents such as a $C_1$ to $C_{20}$ alkyl-substituted aryl group, a $C_1$ to $C_{20}$ alkoxy-substituted aryl group, a $C_1$ to $C_{20}$ haloalkyl-substituted aryl group, a halogen-substituted $C_6$ to $C_{20}$ aryl group, a $C_1$ to $C_{20}$ heterocyclic group, a $C_1$ to $C_{20}$ alkyl-substituted heterocyclic group, a $C_1$ to $C_{20}$ alkoxy-substituted heterocyclic group, a $C_1$ to $C_{20}$ haloalkyl-substituted heterocyclic group, a halogen-substituted $C_1$ to $C_{20}$ heterocyclic group, a $C_7$ to $C_{20}$ arylalkyl group, a $C_1$ to $C_{20}$ alkoxy group, a $C_3$ to $C_{20}$ cycloalkoxy group, a $C_6$ to $C_{20}$ aryloxy group, an amino group which may be monosubstituted or disubstituted with $C_1$ to $C_{20}$ alkyl, an urea group which may be monosubstituted or disubstituted with $C_1$ to $C_{20}$ alkyl, a $C_1$ to $C_{20}$ haloalkyl group, a $C_1$ to $C_{20}$ haloalkoxy group, a silyl group containing $C_1$ to $C_{20}$ hydrocarbon group, a stannyl group containing $C_1$ to $C_{20}$ hydrocarbon group, a nitro group, a halogen atom or the like.

As the above heterocyclic groups, there may be exemplified thienyl, furyl, pyrrolyl, pyrazolyl, isothiazolyl, isoxazolyl, pyridyl, pyrazinyl, pyrimidinyl, indolyl, carbazolyl or the like.

In the present invention, as the cyclopentadienyl compounds, there may be used any of the conventionally known compounds without limitation, as described above. Among these compounds, cyclopentadienyl compounds having a condensed ring on the cyclopentadienyl group are preferred. Further, such alkali metal salts or alkali earth metal salts of cyclopentadienyl compounds as represented by the following general formula (IV) are more preferred.

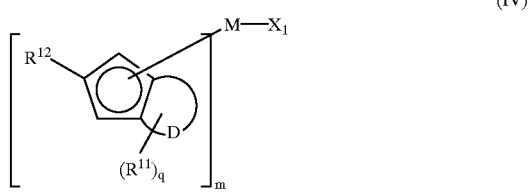

(IV)

wherein $R^{11}$ is a $C_1$ to $C_{20}$ hydrocarbon group or $C_1$ to $C_{20}$ hydrocarbon group containing a nitrogen, oxygen, sulfur, silicon or halogen; $R^{12}$ is a hydrogen atom, a $C_1$ to $C_{10}$ hydrocarbon group or $C_1$ to $C_1$o hydrocarbon group containing a nitrogen, oxygen, sulfur or halogen, a $C_1$ to $C_{18}$ hydrocarbon group containing silicon or a halogen atom; D is a saturated or unsaturated $C_3$ to $C_8$ divalent hydrocarbon group; M is an alkali metal or an alkali earth metal; q is an integer of 0 to 16; m is an integer of 1 or 2; 1 is an integer of 0 or 1; and when m is 2, 1 is 0.

Specific examples of $R^{11}$, $R^{12}$ and D may include substituents appropriately selected from the above-mentioned substituents or combination thereof.

Specific examples of the above-mentioned cyclopentadienyl compounds may include cyclopentadiene, methyl cyclopentadiene, ethyl cyclopentadiene, i-propyl cyclopentadiene, tert-butyl cyclopentadiene, phenyl cyclopentadiene, naphthyl cyclopentadiene, trimethylsilyl cyclopentadiene, 1,2-dimethyl cyclopentadiene, 1,3-dimethyl cyclopentadiene, 1,2,3-trimethyl cyclopentadiene, 1,2,4-trimethyl cyclopentadiene, 1,2,3,4-tetramethyl cyclopentadiene, 1-ethyl-2,4-dimethyl cyclopentadiene, 1-ethyl-3,4-dimethyl cyclopentadiene, 1-tert-butyl-3-methyl cyclopentadiene, 1-i-propyl-3-methyl cyclopentadiene, 1-trimethylsilyl-3-methyl cyclopentadiene, 1,2-dimethyl-4-tert-butyl cyclopentadiene, 1,2-dimethyl-4-trimethylsilyl cyclopentadiene or the like.

Other specific examples of the above-mentioned cyclopentadienyl compounds may include indene, 1-methyl indene, 2-methyl indene, 4-methyl indene, 5-methyl indene, 2-ethyl indene, 2-i-propyl indene, 2-phenyl indene, 2-trimethylsilyl indene, 2,4-dimethyl indene, 2-methyl-4-methoxy indene, 2-methyl-4-i-propyl indene, 2-methyl-4-phenyl indene, 2-methyl-4-naphthyl indene, 2-methyl-4,5-benzindene, 2-ethyl-4-methyl indene, 2-ethyl-4-methoxy indene, 2-ethyl-4-i-propyl indene, 2-ethyl-4-phenyl indene, 2-ethyl-4-naphthyl indene, 2-ethyl-4,5-benzindene, 2,4,7-trimethyl indene, 2-methyl-4-indolyl indene, 2-n-propyl-4-phenathryl indene 4,5,6,7-tetrahydroindene, 2-methyl-4,5,6,7-tetrahydroindene, fluorene or the like.

Still other specific examples of the above-mentioned cyclopentadienyl compounds may include 2,4-dimethyl-1,4-dihydroazulene, 2-methyl-4-tert-butyl-1,4-dihydroazulene, 2-methyl-4-i-propyl-1,4-dihydroazulene, 2-methyl-4-phenyl-1,4-dihydroazulene, 2-methyl-4-naphthyl-1,4-dihydroazulene, 2-ethyl-4-methyl-1,4-dihydroazulene, 2-ethyl-4-tert-butyl-1,4-dihydroazulene, 2-ethyl-4-i-propyl-1,4-dihydroazulene, 2 -ethyl-4-phenyl-1,4-dihydroazulene, 2-ethyl-4-naphthyl-1,4-dihydroazulene, 2,4,4-trimethyl-1,4-dihydroazulene, 2,4,7-trimethyl-1,4-dihydroazulene, 2-ethyl-4,4-dimethyl-1,4-dihydroazulene, 2-ethyl-4,7-dimethyl-1,4-dihydroazulene, 2-i-propyl-4-phenyl-1,4-dihydroazulene, 2-benzyl-4-phenyl-7-i-propyl-1,4-dihydroazulene, 2-methyl-4-(4-chlorophenyl)-1,4-dihydroazulene, 2-methyl-4-(3-trifluoromethylphenyl)-1,4-dihydroazulene, 2-methyl-4-(2-fluorophenyl)-1,4-dihydroazulene, 2-methyl-4-(4-t-butylphenyl)-1,4-dihydroazulene, 2-methyl-4-(4-methoxyphenyl)-1,4-dihydroazulene, 2-methyl-4-(4-dimethylaminophenyl)-1,4-dihydroazulene, 2,4,4-trimethyl-1,4,5,6,7,8-hexahydroazulene or the like.

In the present invention, it is preferred that the cyclopentadienyl group has 1 to 4 substituent groups. Especially, cyclopentadienes which have 2 to 4 substituents, indenes, fluorenes, dihydroazulenes and hexahydroazulenes, are more preferred.

Specific examples of the above-mentioned compounds may include 1,2-dimethyl cyclopentadiene, 1,3-dimethyl cyclopentadiene, 1,2,3-trimethyl cyclopentadiene, 1,2,4-trimethyl cyclopentadiene, 1,2,3,4-tetramethyl cyclopentadiene, 1-ethyl-2,4-dimethyl cyclopentadiene, 1-ethyl-3,4-dimethyl cyclopentadiene, l-tert-butyl-3-methyl cyclopentadiene, 1-i-propyl-3-methyl cyclopentadiene, 1-trimethylsilyl-3-methyl cyclopentadiene, 1,2-dimethyl-4-tert-butyl cyclopentadiene, 1,2-dimethyl-4-trimethylsilyl cyclopentadiene or the like.

Other specific examples of the above-mentioned compounds may include indene, l-methyl indene, 2-methyl indene, 4-methyl indene, 5-methyl indene, 2-ethyl indene, 2-i-propyl indene, 2-phenyl indene, 2-trimethylsilyl indene, 2,4-dimethyl indene, 2-methyl-4-methoxy indene, 2-methyl-4-i-propyl indene, 2-methyl-4-phenyl indene, 2-methyl-4-naphthyl indene, 2-methyl-4,5-benzindene, 2-ethyl-4-methyl indene, 2-ethyl-4-methoxy indene, 2-ethyl-4-i-propyl indene, 2-ethyl-4-phenyl indene, 2-ethyl-4-naphthyl indene, 2,4,7-trimethyl indene, 2-methyl-4-indolyl indene, 2-n-propyl-4-phenathryl indene, 4,5,6,7-tetrahydro indene, 2-methyl-4,5,6,7-tetrahydro indene, fluorene or the like.

Still other specific examples of the above-mentioned compounds may include 2,4-dimethyl-1,4-dihydroazulene, 2-methyl-4-tert-butyl-1,4-dihydroazulene, 2-methyl-4-i-propyl-1,4-dihydroazulene, 2-methyl-4-phenyl-1,4-dihydroazulene, 2-methyl-4-naphthyl-1,4-dihydroazulene, 2-ethyl-4-methyl-1,4-dihydroazulene, 2-ethyl-4-tert-butyl-1,4-dihydroazulene, 2-ethyl-4-i-propyl-1,4-dihydroazulene, 2-ethyl-4-phenyl-1,4-dihydroazulene, 2-ethyl-4-naphthyl-1,4-dihydroazulene, 2,4,4-trimethyl-1,4-dihydroazulene, 2,4,7-trimethyl-1,4-dihydroazulene, 2-ethyl-4,4-dimethyl-1,4-dihydroazulene, 2-ethyl-4,7-dimethyl-1,4-dihydroazulene, 2-i-propyl-4-phenyl-1,4-dihydroazulene, 2-benzyl-4- phenyl-7-i-propyl-1,4-dihydroazulene, 2-methyl-4-(4-chlorophenyl)-1,4-dihydroazulene, 2-methyl-4-(3-trifluoromethylphenyl)-1,4-dihydroazulene, 2-methyl-4-(2-fluorophenyl)-1,4-dihydroazulene, 2-methyl-4-(4-t-butylphenyl)-1,4-dihydroazulene, 2-methyl-4-(4-methoxyphenyl)-1,4-dihydroazulene, 2-methyl-4-(4-dimethylaminophenyl)-1,4-dihydroazulene, 2,4,4-trimethyl-1,4,5,6,7,8-hexahydroazulene or the like.

Meanwhile, as to the above compounds having a dihydroazulene skeleton, "1,4-dihydroazulene" is illustrated as a typical example thereof. However, it is meant that the compounds include (1) compounds having a 2,4-dihydroazulene skeleton, a 3,4-dihyroazulene skeleton, a 3a,4-dihydroazulene skeleton and a 4,8a-dihydroazulene skeleton, or mixtures thereof; (2) compounds having a 1,6-dihydroazulene skeleton, a 2,6-dihyroazulene skeleton, a 3,6-dihydroazulene skeleton, a 3a,6-dihydroazulene skeleton and a 6,8a-dihydroazulene skeleton, or mixtures thereof; and (3) compounds having a 1,8-dihydroazulene skeleton, a 2,8-dihyroazulene skeleton, a 3,8-dihydroazulene skeleton, a 3a,8-dihydroazulene skeleton and a 8,8a-dihydroazulene skeleton, or mixtures thereof.

Also, it is meant that the above compounds having a hexahydroazulene skeleton may include those compounds having in addition to a 1,4,5,6,7,8-hexahydroazulene skeleton, a 2,4,5,6,7,8-hexahydroazulene skeleton, a 3,4,5,6,7,8-hexahydroazulene skeleton, a 3a,4,5,6,7,8-hexahydroazulene skeleton and a 4,5,6,7,8,8a-hexahydroazulene skeleton, or mixtures thereof.

The above-mentioned concepts concerning hydroazulene skeletons are also applicable to the below-mentioned silicon- or germanium-containing organic compound (iv).

The metal salt of cyclopentadienyl compound can be produced by reacting an alkali metal or an alkali earth metal with the cyclopentadienyl compound in an inert solvent. As the inert solvents, there may be used, for example, hexane, benzene, toluene, diethyl ether, dibutyl ether, tetrahydrofuran, or mixed solvents thereof.

The above-mentioned metals can be used in the form of a metal compound. Specific examples of the metal compounds may include hydrides such as lithium hydride, sodium hydride or potassium hydride; metal amides such as lithium-di-i-propyl amide or sodium amide; alkyl metals such as methyl lithium, i-propyl lithium, n-butyl lithium or tert-butyl lithium; aryl metals such as phenyl lithium or naphthyl lithium; alkyl magnesium halides such as ethyl magnesium bromide; dialkyl magnesium such as dibutyl magnesium or butyloctyl magnesium; or the like. The amount of the metal used in the above reaction is usually 0.1 to 2.0 moles, preferably 0.9 to 1.2 moles based on one mole of the cyclopentadienyl compound.

The production reaction for the metal salt of cyclopentadienyl compound may be a salt-forming reaction accompanied with an addition reaction of an alkyl group or aryl group, for example, as described in European Patent No. 697418. More specifically, an alkyl lithium compound or an aryl lithium compound is reacted with an azulene compound in an inert solvent, thereby forming a lithium salt of 1,4-dihydroazulene compound. As the alkyl lithium compounds, there may be used methyl lithium, i-propyl lithium, n-butyl lithium, tert-butyl lithium or the like. As the aryl lithium compounds, there may be used phenyl lithium, naphthyl lithium or the like. Further, as the inert solvents, there may be used hexane, benzene, toluene, diethyl ether, tetrahydrofuran, or mixed solvents thereof.

In the present invention, as the alkyl groups capable of forming alkyl metal salts as the organic metal salt (i), there may be preferably used $C_1$ to $C_{20}$ alkyl groups. Typical examples of the preferable alkyl metal salts may include alkyl lithium such as methyl lithium, n-butyl lithium, sec-butyl lithium, tert-butyl lithium, etc.; dialkyl magnesium such as dibutyl magnesium, butyloctyl magnesium, etc.; alkyl Grignard reagents such as methyl magnesium bromide, ethyl magnesium iodide, n-propyl magnesium bromide, i-propyl magnesium bromide, tert-butyl magnesium chloride, benzyl magnesium chloride, etc.; or the like.

In the present invention, as the aryl groups capable of forming aryl metal salts used as the organic metal salt (i), there may be preferably used a phenyl group, a naphthyl group, a phenanthryl group, an anthryl group or the like. Typical examples of the preferable aryl metal salts may include aryl lithium such as phenyl lithium, naphthyl lithium, phenanthryl lithium, anthryl lithium, etc.; diaryl magnesium such as diphenyl magnesium, etc.; aryl Grignard reagents such as phenyl magnesium bromide, para-tolyl magnesium chloride, etc.; or the like.

In the present invention, as the allyl groups capable of forming allyl metal salts used as the organic metal salt (i), there may be preferably used $C_3$ to $C_{20}$ allyl groups. Typical examples of the preferable allyl metal salts may include allyl lithium such as propenyl lithium, cyclopentadienyl lithium, etc.; diallyl magnesium such as dicyclopentadienyl magnesium, etc.; allyl Grignard reagents such as allyl magnesium chloride, cyclopentadienyl magnesium bromide, etc.; or the like.

In the present invention, as the vinyl groups capable of forming vinyl metal salts used as the organic metal salt (i), there may be preferably used $C_2$ to $C_{20}$ vinyl groups. Typical examples of the preferable vinyl metal salts may include vinyl lithium such as 1-cyclohexenyl lithium, etc.; vinyl Grignard reagents such as vinyl magnesium bromide, etc.; or the like.

In the present invention, as the heterocyclic compounds capable of forming heterocyclic metal salts used as the organic metal salt (i), there may be exemplified thiophenes, pyrroles, furans, pyridines or the like. However, in this case, it is necessary to satisfy such a condition that the metal atom of the organic metal salt (i) is bonded to a carbon atom of the heterocyclic group. Specific examples of such heterocyclic metal salts may include lithio-heterocyclic compounds such as 2-lithio-thiophenes, 2-lithio-pyrroles, 2-lithio-furans, 3-lithio-thiophenes, 3-lithio-pyrroles, 3-lithio-furans, etc.; heterocyclic Grignard reagents such as pyridyl magnesium bromides, thienyl magnesium bromides, pyrrolyl magnesium chlorides, furyl magnesium bromides, etc.; or the like.

The above-mentioned alkyl metal salts, aryl metal salts, allyl metal salts, vinyl metal salts and heterocyclic metal salts can be produced, for example, by the following methods.

In the case of the lithium salts, there may be used (1) a method of subjecting an alkyl lithium or metallic lithium and an organic halogen compound to lithium-halogen exchange reaction; (2) a method of subjecting an organic tin compound, an organic selenium compound or an organic tellurium compound and an alkyl lithium to a transmetallation reaction; (3) a method of reacting a heterocyclic compound with an alkyl lithium; or the like.

In the case of the dialkyl magnesium or the diaryl magnesium, there may be used such methods as described, for example, in U.S. Pat. No. 4,329,301 and European Patent No. 0,157,297. In the case of the alkyl Grignard reagents, the aryl Grignard reagents, the allyl Grignard reagents, the vinyl Grignard reagents and the heterocyclic Grignard reagents, there may be used a typical method of reacting a corresponding organic halide with metallic magnesium in an ether-based solvent such as diethyl ether, tetrahydrofuran or the like. In the case of the vinyl Grignard reagents or the benzyl Grignard reagents such as benzyl magnesium chloride, there may be used a method of reacting a corresponding organic halogen compound with anthracene magnesium dianion.

Next, the silicon (germanium) compound (ii) is explained. As the leaving groups contained in the silicon (germanium) compound (ii), there may be preferably used halogen atoms, substituted or unsubstituted alkyl sulfonyloxy groups or substituted or unsubstituted aryl sulfonyloxy groups, though not particularly restricted thereto. The silicon (germanium) compound may be usually substituted with 1 to 4 substituent groups. In this case, when a plurality of halogen atoms, alkyl sulfonyloxy groups or aryl sulfonyloxy groups are present, these groups may be the same or different.

As substituent groups bonded to the silicon atom or the germanium atom other than the above-mentioned halogen atoms, substituted or unsubstituted alkyl sulfonyloxy groups or substituted or unsubstituted aryl sulfonyloxy groups, there may be exemplified hydrogen, a $C_1$ to $C_{20}$ hydrocarbon group, a $C_1$ to $C_{20}$ hydrocarbon group-substituted silyl group such as trimethylsilyl, a $C_1$ to $C_{20}$ alkoxy group, a $C_6$ to $C_{20}$ aryloxy group or the like. When a plurality of substituent groups are bonded to the silicon atom or the germanium atom, these substituent groups may be the same or different. In addition, a plurality of the substituent groups may form a ring together with the silicon atom or the germanium atom.

In the present invention, as the silicon (germanium) compound (ii), there may be preferably used silicon compound or germanium compound which may be substituted with two halogen atoms, substituted or unsubstituted alkyl sulfonyloxy groups or substituted or unsubstituted aryl sulfonyloxy groups, as represented by the following general formula (V). As more preferable compounds, there may be exemplified such silicon or germanium compounds in which n in the general formula (V) is 0 or 1, and which are substituted with two halogen atoms. As especially preferable compounds, there may be exemplified such silicon compounds in which n in the general formula (V) is 0, and which are substituted with two halogen atoms.

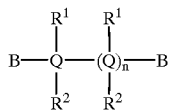

(V)

wherein Q is a silicon atom or a germanium atom; B is a halogen atom, a substituted or unsubstituted alkylsulfonyloxy group or a substituted or unsubstituted arylsulfonyloxy group; $R^1$ and $R^2$ are a substituted or unsubstituted hydrocarbon group or a substituted or unsubstituted cyclic hydrocarbon group formed together with Q to which $R^1$ and $R^2$ are bonded; and n is an integer of 0 to 3.

As the above halogen atoms, there may be exemplified a fluorine atom, a chlorine atom, a bromine atom or an iodine atom. Among them, a chlorine atom and a bromine atom are preferred. As the above substituted or unsubstituted alkyl sulforyloxy groups, there may be exemplified trifluoromethyl sulfonyloxy, mesyloxy, ethyl sulfonyloxy or the like. Among them, trifluoromethyl sulfonyloxy and mesyloxy are preferred. As the above substituted or unsubstituted aryl sulfonyloxy groups, there may be exemplified benzene sulfonyloxy, tosyloxy, p-chlorobenzene sulfonyloxy or the like. Among them, benzene sulfonyloxy and tosyloxy are preferred.

As the above hydrocarbon groups, there may be exemplified $C_1$ to $C_{20}$ hydrocarbons groups. Specific examples of the hydrocarbon groups may include alkyl groups such as methyl, ethyl, n-propyl, i-propyl, n-butyl, sec-butyl, tert-butyl, pentyl, hexyl, etc.; cycloalkyl groups such as cyclopropyl, cyclohexyl, etc.; alkenyl groups such as vinyl, 2-butene-2-yl, etc.; alkynyl groups such as ethynyl, etc.; aryl groups such as phenyl, tosyl, xylyl, naphthyl, etc.; or the like.

Also, the above hydrocarbon groups may be substituted with a halogen atom such as a fluorine atom, a chlorine atom, a bromine atom or an iodine atom; an alkoxy group such as methoxy, ethoxy, n-propoxy, i-propoxy, etc.; an aryloxy group such as phenoxy, tosyloxy, xylyloxy, etc.; an amino group such as amino, dimethylamino, etc.; a trialkylsilyl group such as trimethylsilyl, etc.; or the like. Incidentally, $R^1$ and $R^2$ may be the same or different.

In the present invention, specific examples of the silicon (germanium) compounds may include the following compounds (1) to (3):

(1) tetrahalogenated silicon compounds such as tetrachlorosilane, tetrabromosilane, etc.; trihalogenated silicon comoounds such as methyltrichlorosilane, phenyltrichlorosilane, methyltribromosilane, phenyltribromosilane, etc.; dihalogenated silicon compounds such as dimethyldichlorosilane, diethyldichlorosilane, di-n-propyl dichlorosilane, di-tert-butyl dichlorosilane, dicyclopropyl dichlorosilane, dicyclohexyl dichlorosilane, diphenyl dichlorosilane, bis(4-methylphenyl) dichlorosilane, bis(2,6-dimethylphenyl) dichlorosilane, (methyl)(phenyl) dichlorosilane, (4-chlorophenyl)(methyl) dichlorosilane, (4-fluorophenyl)(methyl) dichlorosilane, (chloromethyl)(methyl) dichlorosilane, 1,1-dichloro-1-silacyclobutane, 1,1-dichloro-1-silacyclopentane, 1,1-dichloro-1-silacyclohexane, 1,1-dichloro-2,3,4,5-tetramethyl-1-silacyclopenta-2,4-diene, dimethyl dibromosilane, diethyl dibromosilane, di-n-propyl dibromosilane, di-tert-butyl dibromosilane, dicyclopropyl dibromosilane, dicyclohexyl dibromosilane, diphenyl dibromosilane, bis(4-methylphenyl) dibromosilane, bis(2,6-dimethylphenyl) dibromosilane, (methyl)(phenyl) dibromosilane, 1,1-dibromo-1-silacyclobutane, 1,1-dibromo-1-silacyclopentane, 1,1-dibromo-1-silacyclohexane, 1,1-dibromo-2,3,4,5 -tetramethyl-1-silacyclopenta-2,4-diene, etc.; or corresponding germanium compounds.

(2) monohalogenated silicon compounds such as trimethylchlorosilane, triethylchlorosilane, triphenylchlorosilane, tert-butyldimethylchlororsilane, dimethylphenylchlorosilane, trimethylbromosilane, triethylbromosilane, triphenylbromosilane, tert-butyldimethylbromosilane, dimethylphenylbromosilane, etc.; disilane compounds such as 1,1,2,2-tetramethyl-1,2-dichlorordisilane, etc.; or corresponding germanium compounds.

(3) tert-butyl-dimethylsilyl trifluoromethane sulfonate, trimethylsilyl trifluoromethane sulfonate, triethylsilyl trifluoromethane sulfonate, tri-i-propylsilyl trifluoromethane sulfonate, diethyl-i-propylsilyl trifluoromethane sulfonate, trimethylsilyl nonafluoro-1-butane sulfonate, di-i-propylsilyl bis(trifluoromethane sulfonate), di-tert-butylsilyl bis(trifluoromethane sulfonate), trimethylsilyl methane sulfonate, trimethylsilyl benzene sulfonate, dimethylsilyl bis(trifluoromethane sulfonate), or the like.

Next, the nitrogen-containing aromatic heterocyclic compound (iii) is explained. In general, nitrogen-containing heterocyclic compounds are classified into aliphatic compounds (nitrogen-containing aliphatic heterocyclic compounds) such as, for example, 1,4-diazabicyclo[2,2,2]octane, 1,8-diazabicyclo[5,4,0]-7-undecene, etc., and aromatic compounds (nitrogen-containing aromatic heterocyclic compounds) used in the present invention. However, the aimed objects of the present invention cannot be accomplished by using the nitrogen-containing aliphatic heterocyclic compounds.

In the present invention, as the nitrogen-containing aromatic heterocyclic compounds, there may be preferably used, for example, at least one compound selected from the group consisting of pyrroles, pyrazoles, imidazoles, triazoles, tetrazoles, pyridines, pyridazines, indolizines, pyrimidines, pyrazines, symmetric triazines, asymmetric triazines, thiazoles, isothiazoles, oxazoles, isoxazoles, indoles, isoindoles, 1H-indazoles, purines, benzo[d]isoxazoles, benzo[d]isothiazoles, benzo[d]imidazoles, benzo[d]oxazoles, benzo[d]thiazoles, cuinolines, isoquinolines, cinnolines, phthalazines, naphthyridines, quinoxalines, quinazolines, pteridines, carbazoles, β-carbolines, phenanthridines, acridines, perimidines, phenathrolines, phenazines and phenarsazines.

As substituent groups of the above nitrogen-containing aromatic heterocyclic compounds, there may be exemplified $C_1$ to $C_{20}$ alkyl groups such as methyl, ethyl, n-propyl, i-propyl, n-butyl, sec-butyl, tert-butyl, pentyl, hexyl, etc.; $C_3$ to $C_{20}$ cycloalkyl groups such as cyclopropyl, cyclohexyl, etc.; $C_2$ to $C_{20}$ alkenyl groups such as vinyl, butene-yl, etc.; $C_2$ to $C_{20}$ alkynyl groups such as ethynyl, etc.; $C_6$ to $C_{20}$ aryl groups such as phenyl, tosyl, xylyl, naphthyl, etc.; $C_7$ to $C_{20}$ arylalkyl groups such as benzyl, etc.; $C_1$ to $C_{20}$ alkoxy groups such as methoxy, ethoxy, n-propoxy, i-propoxy, etc.; $C_3$ to $C_{20}$ cycloalkoxy groups such as cyclopropoxy, cyclohexyloxy, etc.; $C_6$ to $C_{20}$ aryloxy groups such as phenoxy, etc.; or the like.

As other substituent groups of the above nitrogen-containing aromatic heterocyclic compounds, there may be exemplified a hydroxy group; a thiol group; $C_1$ to $C_{20}$ alkylthio groups such as methylthio, etc.; $C_2$ to $C_{20}$ acyl groups such as acetyl, etc.; $C_2$ to $C_{20}$ acyloxy groups such as acetoxy, etc.; $C_1$ to $C_{20}$ alkoxy-substituted carbonyl groups such as methoxy carbonyl, ethoxy carbonyl, tert-butoxy carbonyl, etc.; amino groups which may be mono- or di-substituted with a $C_1$ to $C_{20}$ alkyl group, such as amino, monomethylamino, dimethylamino, diethylamino, etc.; $C_1$ to $C_{20}$ haloalkyl groups such as monofluoromethyl, difluoromethyl, trifluoromethyl, pentafluoroethyl, etc.; $C_1$ to $C_{20}$ haloalkoxy groups such as trifluoromethoxy, etc.; $C_1$ to $C_{20}$ trialkylsilyl groups such as trimethylsilyl, triethylsilyl, tert-butyl-dimethylsilyl, etc.; a nitro group; a nitrile group; halogen atoms such as a fluorine atom, a chlorine atom, a bromine atom or an iodine atom; or the like. These substituent groups may be further substituted with the above-mentioned substituent groups. In addition, these substituent groups may be bonded to each other to form a ring. Specific examples of the above nitrogen-containing aromatic heterocyclic compounds may include the following compounds (1) to (9).

(1) pyrroles such as pyrrole, 1-methyl pyrrole, 2-methyl pyrrole, 3-methyl pyrrole, etc.; pyrazoles such as pyrazole, 1-methyl pyrazole, 1-phenyl pyrazole, 3-methyl pyrazole, 1-phenyl-3-methyl pyrazole, 1,3-dimethyl pyrazole, 1,3,5-trimethyl pyrazole, etc.; imidazoles such as imidazole, 1-methyl imidazole, 2-methyl imidazole, 4-methyl imidazole, 4-phenyl imidazole, 1-methyl-2-(1-piperazinyl) imidazole, 1,5-dimethyl imidazole, 3,5-dimethyl imidazole, etc.; triazoles such as 1,2,3-triazole, 1-methyl-1,2,3-triazole, 2-methyl-1,2,3-triazole, 1,2,4-triazole, 3-methyl-1,2,4-triazole, 3-amino-1,2,4-triazole, 3-chloro-1,2,4-triazole, benzotriazole, etc.; or tetrazoles such as tetrazole, 5-amino tetrazole, 5-chloro tetrazole, 1,5-pentamethylene tetrazole, etc., (2) pyridines such as pyridine, 2-methyl pyridine, 3-methyl pyridine, 4-methyl pyridine, 2-ethyl pyridine, 3-ethyl pyridine, 4-ethyl pyridine, 2-i-propyl pyridine, 3-i-propyl pyridine, 4-i-propyl pyridine, 2-tert-butyl pyridine, 3-tert-butyl pyridine, 4-tert-butyl pyridine, 2-phenyl pyridine, 3-phenyl pyridine, 4-phenyl pyridine, 2-vinyl pyridine, 3-vinyl pyridine, 4-vinyl pyridine, 2-dimethylamino pyridine, 3-dimethylamino pyridine, 4-dimethylamino pyridine, 2-methoxy pyridine, 3-methoxy pyridine, 4-methoxy pyridine, 2-methylthio pyridine, 3-methylthio pyridine, 4-methylthio pyridine, 2-chloro pyridine, 3-chloro pyridine, 4-chloro pyridine, 2-cyano pyridine, 3-cyano pyridine, 4-cyano pyridine, 2-nitro pyridine, 3-nitro pyridine, 4-nitro pyridine, 4-benzyloxy pyridine, 2,6-lutidine, 1-H-1,2,3-triazolo[4,5-b]pyridine, etc., (3) pyridazines such as pyridazine, 4-methyl pyridazine, 4-phenyl pyridazine, pyradino[2,3-b]pyridazine, etc.; indolizines such as indolizine, 1-methyl indolizine, etc.; pyrimidines such as pyrimidine, 4-methyl pyrimidine, 2-dimethylamino pyrimidine, 4-dimethylamino pyrimidine, 5-amino pyrimidine, 4,6-dichloro pyrimidine, 4,6-dimethyl pyrimidine, 4,6-dimethoxy pyrimidine, 1,2,4-triazolo[1,5-a]pyrimidine, etc.; pyrazines such as pyrazine, 2-methyl pyrazine, 2-methoxy pyrazine, 2-methylthio pyrazine, etc.; symmetric triazines such as 1,3,5-triazine, 2,4,6-trimethoxy-1,3,5-triazine, etc.; or asymmetric triazines such as 1,2,4-triazine, imidazo[1,2-b][1,2,4]triazine, etc., (4) thiazoles such as thiazole, 2-methyl thiazole, 2-methyl-5-ethoxy thiazole, 2,4-dimethyl thiazole, 2-amino thiazole, 2-amino-4,5-dimethyl thiazole, imidazo[2,1-b]thiazole, 2,1,3-benzo thiadiazole, etc.; isothiazoles such as isothiazole, 3-methyl-isothiazole, 5-methyl-isothiazole, 4-phenyl-isothiazole etc.; oxazoles such as oxazole, 2-methyl oxazole, 2,5-dimethyl oxazole, 2,4-dimethyl oxazole, etc.; or isoxazoles such as isoxazole, 4-methyl-isooxazole, 5-methyl-isooxazole, 3-phenyl-isooxazole, 5-phenyl-isooxazole, 3,5-diphenyl-isooxazole etc., (5) indoles such as indole, 1-methyl indole, 2-methyl indole, 3-methyl indole, 5-methoxy-6-methyl indole, 2,3-dimethyl indole, 2,7-dimethyl indole, 2-dimethylaminomethyl indole, etc.; isoindoles such as isoindole, 1-methyl isoindole, etc.; or 1H-indazoles such as 1H-indazole, 5-nitro-1H-indazole, etc., (6) purines such as purine, 7-methyl purine, adenine, 2,6-dimethyl adenine, etc.; benzo[d]isoxazoles such as benzo[d]isoxazole, 3-methyl benzo[d]isoxazole, 5-methyl benzo[d]isoxazole, 3-benzyl benzo[d]isoxazole, 3-methyl-6-bromo benzo[d]isoxazole, etc.; benzo[d]isothiazoles such as benzo[d]isothiazole, 5-methyl benzo[d]isothiazole, etc.; benzo[d]imidazoles such as benzo[d]imidazole, 1-methyl benzo[d]imidazole, 2-methyl benzo[d]imidazole, etc.; benzo[d]oxazoles such as benzo[d]oxazole, 2-methyl benzo[d]oxazole, etc.; or benzo[d]thiazoles such as benzo[d]thiazole, 2-phenyl benzo[d]thiazole, 2-ethoxy benzo[d]thiazole, 2-amino benzo[d]thiazole, 2-amino-6-methyl benzo[d]thiazole, selenazolo[5,4-f]benzo[d]thiazole, etc., (7) quinolines such as quinoline, 2-methyl quinoline, 3-methyl quinoline, 4-methyl quinoline, 5-methyl quinoline, 6-methyl quinoline, 7-methyl quinoline, 8-methyl quinoline, 4-dimethylamino quinoline, 4-methoxy quinoline, 4-methylthio quinoline, 2-cyanomethyl quinoline, 2,4- dimethyl quinoline, 7,8-benzo quinoline, s-triazolo[4,3-a] quinoline, etc.; or isoquinolines such as isoquinoline, chloroisoquinoline, benzo[h]isoquinoline, etc., (8) cinnolines such as cinnoline, 4-methoxy cinnoline, 4-dimethylamino cinnoline, furano[3,4-c]cinnoline, etc.; phthalazines such as phthalazine, 1-methylthio phthalazine, 5-chloro phthalazine, 1-dicyanomethyl phthalazine, etc.; naphthyridines such as naphthyridine, 1-methyl naphthyridine, etc.; quinoxalines such as quinoxaline, 2-methyl quinoxaline, 2-methoxy quinoxaline, 2-dimethylamino quinoxaline, etc.; quinazolines such as quinazoline, 2-methoxy quinazoline, 4-methoxy quinazoline, 4-methyl quinazoline, etc.; or pteridines such as pteridine, 2-methyl pteridine, etc., (9) carbazoles such as carbazole, 9-methyl carbazole, 4H-pyrazino[2,3-b]carbazole, 7H-pyrazino[2,3-b]carbazole, etc.; β-carbolines such as β-carboline, 9-methyl-β-carboline, etc.; phenanthridines such as phenanthridine, 6-amino phenanthridine, 6-methoxy phenanthridine, etc.; acridines such as acridine, 2-methyl acridine, 4-methyl acridine, 9-methyl acridine, 2-methoxy acridine, 4-methoxy acridine, 9-methoxy acridine, etc.; perimidines such as perimidine, 1-methyl perimidine, etc.; phenathrolines such as phenathroline, 4-methyl phenathroline, etc.; phenazines such as phenazine, 1-methyl phenazine, etc.; or phenarsazines such as phenarsazine, 1-methyl phenarsazine, etc.

Among these nitrogen-containing aromatic heterocyclic compounds, 4-dimethylamino pyridine, imidazole, 1-methyl imidazole, benzo[d]imidazole, 1-methyl benzo[d]imidazole, isoxazole, 1,2,4-triazole and tetrazole are especially preferred.

In accordance with the present invention, the organic metal salt (i) is reacted with the silicon (germanium) compound (ii) in the presence of the nitrogen-containing aromatic heterocyclic compound (iii). In order to effectively proceed the above reaction, it is preferred that the reaction be conducted in a solution or a suspension.

As the reaction solvents, there may be used any solvents as long as they are substantially inert to the above reaction. Specific examples of the reaction solvents may include hydrocarbon-based solvents such as petroleum ethers, pentane, n-hexane, cyclohexane, heptane, benzene, toluene, etc.; ether-based solvents such as diethyl ether, di-i-propyl ether, tetrahydrofuran, dioxane, anisole, methoxy ethane, ethylene glycol dimethyl ether, diethylene glycol dimethyl ether, etc.; or mixed solvents comprising any optional combination thereof. Among these solvents, ether-based solvents or mixed solvents comprising the ether-based solvent and the hydrocarbon-based solvent are preferred. Especially, diethyl ether, di-i-propyl ether, tetrahydrofuran, or mixed solvents comprising these solvents and n-hexane, cyclohexane, heptane or toluene, are more preferred.

The amount of the silicon (germanium) compound (ii) used is usually 0.1 to 10 moles, preferably 0.2 to 5 moles based on one mole of the organic metal salt (i). The nitrogen-containing aromatic heterocyclic compound (iii) may be preferably used in a catalytic amount. More specifically, the nitrogen-containing aromatic heterocyclic compound (iii) may be used in an amount of usually 0.001 to 1 mole, preferably 0.001 to 0.25 mole, more preferably 0.005 to 0.2 mole based on one mole of the silicon (germanium) compound (ii).

The reaction temperature may be appropriately selected from the range of usually from −78° C. to a boiling point of the solvent used, preferably −60° C. to 100° C., more preferably −30° C. to 80° C. The reaction pressure is usually an ordinary pressure though not particularly restricted thereto. The reaction atmosphere is usually an inert gas atmosphere such as nitrogen, argon or the like, though not particularly restricted thereto.

The above reaction may be carried out by either a batch method or a continuous method. In this case, the silicon (germanium) compound (ii) or a solution thereof may be dropped into a solution or a suspension containing the organic metal salt (i). Conversely, a solution or a suspension containing the organic metal salt (i) may be dropped into the silicon (germanium) compound (ii) or a solution thereof.

For example, in the case where two kinds of organic metal salts (α) and (β) which are different in A of the above general formula (I) from each other, are used as the organic metal salt (i), the organic metal salt (α) is first reacted with the silicon (germanium) compound (ii), and then the resultant reaction product which may be subjected to the below-mentioned purification treatment in advance, is reacted with the organic metal salt (β), thereby producing a silicon- or germanium-containing organic compound having different substituent groups.

The nitrogen-containing aromatic heterocyclic compound (iii) may be previously mixed either with a solution or a suspension of the organic metal salt (i), or with the silicon (germanium) compound (ii) or a solution thereof. Alternatively, after mixing the organic metal salt (i) with the silicon (germanium) compound (ii), the nitrogen-containing aromatic heterocyclic compound (iii) may be added to the mixture.

The reaction time may be varied depending upon kinds of organic metal salt (i), silicon (germanium) compound (ii) and nitrogen-containing aromatic heterocyclic compound (iii) used, molar ratios therebetween, kind of solvent used and reaction temperature. The reaction time is usually one minutes to one week, preferably 5 minutes to 4 days, more preferably 10 minutes to 2 days.

After completion of the reaction, the reaction product may be purified by various methods such as extraction, acid- or alkali-washing, washing with a poor solvent, concentration, filtration, chromatography, distillation, sublimation, recrystallization or the like, thereby obtaining the aimed silicon- or germanium-containing organic compound. Alternatively, the reaction product may be immediately transferred to subsequent reactions (e.g., production reaction of metallocene catalysts) without adopting the purifying steps.

The production process according to the present invention may be applied, for example, to the production of various silicon- or germanium-containing organic compounds (iv) such as tetramethyl silane, tert-butyl dimethylsilyl chloride, tert-butylsilyl trichloride, 1,1-dimethylpropylmethyl dichlorosilane, tert-butyldiphenylsilyl chloride, tert-butylmethyl dichlorosilane, tert-butylmethylphenyl chlorosilane, tert-butylvinyl dichlorosilane, 1,1-dimethylbenzyldimethyl chlorosilane, 1,1-dimethylpropyl trichlorosilane or the like. In particular, the production process according to the present invention can be preferably applied to the production of silyl-substituted or germyl-substituted cyclopentadienyl compounds.

As the above-mentioned silyl-substituted or germyl-substituted cyclopentadienyl compounds, there may be exemplified monocyclopentadienyl silane compounds, dicyclopentadienyl silane compounds, dicyclopentadienyl disilane compounds, tricyclopentadienyl silane compounds, tetracyclopentadienyl silane compounds, monocyclopentadienyl germane compounds, dicyclopentadienyl germane compounds, dicyclopentadienyl digermane compounds, tricyclopentadienyl germane compounds, tetracyclopentadienyl germane compounds or the like. Specific examples of these compounds may include the following compounds (1) to (11). Meanwhile, in the following descriptions, although only silicon compounds are illustrated for convenience, it should be understood that such corresponding germane compounds as given by replacing "silane" of all the silane compounds with "germane" are also involved in the scope of the present invention.

<Monocyclopentadienyl Silicon Compounds>

(1) cyclopentadienyl trimethylsilane, cyclopentadienyl triethylsilane, cyclopentadienyl tri-i-propylsilane, cyclopentadienyl triphenylsilane, cyclopentadienyl-tert-butyl dimethylsilane, (cyclopentadienyl)(dimethyl)(phenyl) silane, (cyclopentadienyl)(diphenyl)(methyl) silane, 2-methyl cyclopentadienyl trimethylsilane, 3-methyl cyclopentadienyl trimethylsilane, 2-methyl cyclopentadienyl triphenylsilane, 3-methyl cyclopentadienyl triphenylsilane, 3-tert-butyl cyclopentadienyl trimethylsilane, 3,4-dimethyl cyclopentadienyl trimethylsilane, 2,3,4-trimethyl cyclopentadienyl trimethylsilane, 2,3,5-trimethyl cyclopentadienyl trimethylsilane, 2,3,5-trimethyl cyclopentadienyl dimethylchlorosilane, (2,3,5-trimethyl cyclopentadienyl)(methyl)(phenyl) chlorosilane, 2,3,5-trimethyl cyclopentadienyl diphenylchlorosilane, 2,3,4,5-tetramethyl cyclopentadienyl trimethylsilane or 2,3,4,5-tetramethyl cyclopentadienyl dimethylchlorosilane, (2) 1-indenyl trimethylsilane, 1-indenyl triphenylsilane, 2-methyl-1-indenyl trimethylsilane, 2-methyl-1-indenyl triphenylsilane, 2-methyl-1-indenyl dimethylchlorolsilane, (2-methyl-1-indenyl)(methyl)(phenyl) chlorosilane, 2-methyl-i-indenyl diphenylchlorosilane, 4-methyl-1-indenyl trimethylsilane, 5-methyl-1-indenyl trimethylsilane or 2-ethyl-1-indenyl trimethylsilane, (3) 2-methyl-4-i-propyl-1-indenyl trimethylsilane, 2-methyl-4-i-propyl-1-indenyl dimethylchlorosilane, (2-methyl-4-i-propyl-1-indenyl)(methyl)(phenyl) chlorosilane, 2-methyl-4-i-propyl-1-indenyl diphenylchlorosilane, 2-methyl-4-phenyl-1-indenyl trimethylsilane, 2-methyl-4-phenyl-1-indenyl dimethylchlorosilane, (2-methyl-4-phenyl-1-indenyl)(methyl)(phenyl) chlorosilane, 2-methyl-4-phenyl-1-indenyl diphenylchlorosilane, 2-methyl-4-naphthyl-1-indenyl trimethylsilane, 2-methyl-4-naphthyl-1-indenyl dimethylchlorosilane, (2-methyl-4-naphthyl-1-indenyl)(methyl)(phenyl) chlorosilane, 2-methyl-4-naphthyl-1-indenyl diphenylchlorosilane, 2-methyl-4,5-benzo-1-indenyl trimethylsilane, 2-methyl-4,5-benzo-1-indenyl dimethylchlorosilane, (2-methyl-4,5-benzo-1-indenyl) (methyl) (phenyl) chlorosilane or 2-methyl-4,5-benzo-1-indenyl diphenylchlorosilane, (4) 2-methyl-4-i-propyl-1,4-dihydro-1-azulenyl trimethylsilane, 2-methyl-4-i-propyl-1,4-dihydro-1-azulenyl dimethylchlorosilane, (2-methyl-4-i-propyl-1,4-dihydro-1-azulenyl)(methyl)(phenyl) chlorosilane, 2-methyl-4-i-propyl-1,4-dihydro-1-azulenyl diphenylchlorosilane, 2-methyl-4-phenyl-1,4-dihydro-1-azulenyl trimethylsilane, 2-methyl-4-phenyl-1,4-dihydro-1-azulenyl dimethylchlorosilane, (2-methyl-4-phenyl-1,4-dihydro-1-azulenyl)(methyl)(phenyl) chlorosilane, 2-methyl-4-phenyl-1,4-dihydro-1-azulenyl diphenylchlorosilane, 2-methyl-4-naphthyl-1,4-dihydro-1-azulenyl trimethylsilane, 2-methyl-4-naphthyl-1,4-dihydro-1-azulenyl dimethylchlorosilane, (2-methyl-4-naphthyl-1,4-dihydro-1-azulenyl)(methyl)(phenyl) chlorosilane, 2-methyl-4-naphthyl-1,4-dihydro-1-azulenyl diphenylchlorosilane, 2-ethyl-4-phenyl-1,4-dihydro-1-azulenyl trimethylsilane, 2-ethyl-4-phenyl-1,4-dihydro-1-azulenyl dimethylchlorosilane, 2-ethyl-4-phenyl-1,4-dihydro-1-azulenyl methylphenylchlorosilane or 2-ethyl-4-phenyl-1,4-dihydro-1-azulenyl diphenylchlorosilane.

<Dicyclopentadienyl Silicon Compound>

(5) dicyclopentadienyl dimethylsilane, dicyclopentadienyl diethylsilane, dicyclopentadienyl di-i-propylsilane, dicyclopentadienyl diphenylsilane, dicyclopentadienyl di-tert-butyl silane, (dicyclopentadienyl)(methyl)(phenyl) silane, dicyclopentadienyl diphenylsilane, bis(2-methyl cyclopentadienyl) dimethylsilane, bis(3-methyl cyclopentadienyl) dimethylsilane, bis(2-methyl cyclopentadienyl) diphenylsilane, bis(3,4-dimethyl cyclopentadienyl) dimethylsilane, bis(2,3,4-trimethyl cyclopentadienyl) dimethylsilane, bis(2,3,5-trimethyl cyclopentadienyl) dimethylsilane, bis(2,3,5-trimethyl cyclopentadienyl) methylchlorosilane, bis(2,3,5-trimethyl cyclopentadienyl)(methyl)(phenyl) silane, bis(2,3,5-trimethyl cyclopentadienyl) diphenylsilane, bis(2,3,4,5-tetramethyl cyclopentadienyl) dimethylsilane or bis(2,3,4,5-tetramethyl cyclopentadienyl) methylchlorosilane, (6) di(1-indenyl) dimethylsilane, di(1-indenyl) diphenylsilane, bis(2-methyl-1-indenyl) dimethylsilane, bis(2-methyl-1-indenyl) diphenylsilane, bis(2-methyl-1-indenyl) methylchlorosilane, bis(2-methyl-1-indenyl)(methyl)(phenyl) silane, bis(2-methyl-1-indenyl) phenylchlorosilane, bis(4-methyl-1-indenyl) dimethylsilane, bis(5-methyl-1-indenyl) dimethylsilane or bis(2-ethyl-1-indenyl) dimethylsilane, (7) bis(2-methyl-4-i-propyl-1-indenyl) dimethylsilane, bis(2-methyl-4-i-propyl-1-indenyl) methylchlorosilane, bis (2-methyl-4-i-propyl-1indentyl) (methyl) (phenyl) silane bis (2-methyl-4-i-propyl-1-indenyl) diphenylsilane, bis(2-methyl-4-phenyl-1-indenyl) dimethylsilane, bis(2-methyl-4-phenyl-1-indenyl) methylchlorosilane, bis(2-methyl-4-phenyl-1-indenyl)(methyl)(phenyl) silane, bis(2-methyl-4-phenyl-1-indenyl) diphenylsilane, bis(2-methyl-4-naphthyl-1-indenyl) dimethylsilane, bis(2-methyl-4-naphthyl-1-indenyl) methylchlorosilane, bis(2-methyl-4-naphthyl-1-indenyl)(methyl)(phenyl) silane, bis(2-methyl-4-naphthyl-1-indenyl) diphenylsilane, bis(2-methyl-4,5-benzo-1-indenyl) dimethylsilane, bis(2-methyl-4,5-benzo-1-indenyl) methylchlorosilane, bis(2-methyl-4,5-benzo-1-indenyl) (methyl) (phenyl) silane, bis(2-methyl-4,5-benzo-1-indenyl) diphenylsilane, bis(2-methyl-4-indolyl-1-indenyl) dimethylsilane or bis(2,4,7-trimethyl-1-indenyl) dimethylsilane, (8) bis(2-methyl-4-i-propyl-1,4-dihydro-1-azulenyl) dimethylsilane, bis(2-methyl-4-i-propyl-1,4-dihydro-1-azulenyl) methylchlorosilane, bis(2-methyl-4-i-propyl-1,4-dihydro-1-azulenyl)(methyl)(phenyl) silane, bis(2-methyl-4-i-propyl-1,4-dihydro-1-azulenyl) diphenylsilane, bis(2-methyl-4-phenyl-1,4-dihydro-1-azulenyl) dimethylsilane, bis(2-methyl-4-phenyl-1,4-dihydro-1-azulenyl) methylchlorosilane, bis(2-methyl-4-phenyl-1,4-dihydro-1-azulenyl)(methyl)(phenyl) silane, bis(2-methyl-4-phenyl-1,4-dihydro-1-azulenyl) diphenylsilane, bis(2-methyl-4-naphthyl-1,4-dihydro-1-azulenyl) dimethylsilane, bis(2-methyl-4-naphthyl-1,4-dihydro-1-azulenyl) methylchlorosilane, bis(2-methyl-4-naphthyl-1,4-dihydro-1-azulenyl)(methyl)(phenyl) silane, bis(2-methyl-4-naphthyl-1,4-dihydro-1-azulenyl) diphenylsilane, bis(2-ethyl-4-phenyl-1,4-dihydro-1-azulenyl) dimethylsilane, bis(2-ethyl-4-phenyl-1,4-dihydro-1-azulenyl)(methyl)(phenyl) silane, bis(2-ethyl-4-phenyl-1,4-dihydro-1-azulenyl) diphenylsilane, bis(2-benzyl-4-phenyl-7-i-propyl-1,4-dihydro-1-azulenyl) dimethylsilane, bis{2-methyl-4-(4-chlorophenyl)-1,4-dihydro-1-azulenyl} dimethylsilane, bis{2-methyl-4-(3-trifluoromethylphenyl)-1,4-dihydro-1-azulenyl} dimethylsilane, bis{2-methyl-4-(2

-fluorophenyl)-1,4-dihydro-1-azulenyl} dimethylsilane, bis{2-methyl-4-(4-t-butylphenyl)-1,4-dihydro-1-azulenyl} dimethylsilane, bis{2-methyl-4-(4-methoxyphenyl)-1,4-dihydro-1-azulenyl} dimethylsilane, bis{2-methyl-4-(4-dimethylaminophenyl)-1,4-dihydro-1-azulenyl} dimethylsilane, bis(2,4,4-trimethyl-1,4,5,6,7,8-hexahydro-1-azulenyl) dimethylsilane, bis(2-methyl-4-phenyl-1,4-dihydro-1-azulenyl)(4-chlorophenyl)(methyl) silane, bis(2-methyl-4-phenyl-1,4-dihydro-1-azulenyl)(4-fluorophenyl)(methyl) silane or bis(2-methyl-4-phenyl-1,4-dihydro-1-azulenyl)(chloromethyl)(methyl) silane, (9) (1-fluorenyl)(cyclopentadienyl) dimethylsilane, (1-fluorenyl)(3-methyl cyclopentadienyl) dimethylsilane, (1-fluorenyl)(3-tert-butyl cyclopentadienyl) dimethylsilane, (3-tert-butyl-1-indenyl)(3-tert-butyl cyclopentadienyl) dimethylsilane, (3-tert-butyl-1-indenyl)(3-tert-butyl cyclopentadienyl)(methyl)(phenyl) silane, (3-tert-butyl-1-indenyl)(3-tert-butyl cyclopentadienyl) diphenylsilane, (2methyl-4-phenyl-1-indenyl)(2,3,5-trimethyl cyclopentadienyl) dimethylsilane, (2-methyl-4-phenyl-1-indenyl)(2,3,5-trimethyl cyclopentadienyl)(methyl)(phenyl) silane, (2-methyl-4-phenyl-1-indenyl)(2,3,5-trimethyl cyclopentadienyl) diphenylsilane, (2-ethyl-4-phenyl-1-indenyl)(2,3,5-trimethyl cyclopentadienyl) dimethylsilane, (2-ethyl-4-phenyl-1-indenyl)(2,3,5-trimethyl cyclopentadienyl)(methyl)(phenyl) silane, (2-ethyl-4-phenyl-1-indenyl)(2,3,5-trimethyl cyclopentadienyl) diphenylsilane, (2 -methyl-4,5-benzo-1-indenyl)(2,3,5-trimethyl cyclopentadienyl) dimethylsilane, (2-methyl-4,5-benzo-1-indenyl)(2,3,5-trimethyl cyclopentadienyl) diphenylsilane, (2-methyl-4,5-benzo-1-indenyl)(2,3,5-trimethyl cyclopentadienyl)(methyl)(phenyl) silane, (2-methyl-4,5-benzo-1-indenyl)-(2-methyl-4-phenyl-1-indenyl) dimethylsilane, (2-methyl-4-phenyl-1,4-dihydro-1-azulenyl)(2,3,5-trimethyl cyclopentadienyl)(methyl) (phenyl) silane, (2-methyl-4-phenyl-1,4-dihydro-1-azulenyl)(2,3,5-trimethyl cyclopentadienyl) dimethylsilane, (2-methyl-4-phenyl-1,4-dihydro-1-azulenyl)(2,3,5-trimethyl cyclopentadienyl) diphenylsilane or 1,2-bis(2-methyl-4-phenyl-1,4-dihydro-1-azulenyl)-1,1,2,2-tetramethyl disilane.

<Tricyclopentadienyl Silicon Compound>

(10) tri(cyclopentadienyl) silane, tri(cyclopentadienyl) methylsilane, tri(cyclopentadienyl) phenylsilane, tri (cyclopentadienyl) chlorosilane, tri(1-indenyl) silane, tri(1-indenyl) methylsilane, tri(1-indenyl) phenylsilane, tri(1-indenyl) chlorosilane, tris(2-methyl-1-indenyl) silane, tris (2-methyl-1-indenyl) methylsilane, tris(2-methyl-1-indenyl) phenylsilane, tris(2-methyl-1-indenyl) chlorosilane, tris(2-methyl-4-phenyl-1-indenyl) silane, tris(2-methyl-4-phenyl-1-indenyl) methylsilane or tris(2-methyl-4-phenyl-1-indenyl) chlorosilane.

<Tetracyclopentadienyl Silicon Compound>

(11) tetra(cyclopentadienyl) silane, tetra(1-indenyl) silane, tetrakis(2-methyl-1-indenyl) silane, tetrakis(2 -methyl-4-phenyl-1-indenyl) silane or tetrakis(2-methyl-4-phenyl-1,4-dihydro-1-azulenyl) silane.

Next, the process for producing a transition metal complex according to the present invention, is explained. In accordance with the present invention, the transition metal complex can be produced by reacting the above-obtained silicon- or germanium-containing organic compound (iv) (dicyclopentadienyl silicon compound or cyclopentadienyl germanium compound) with a transition metal compound. A typical reaction path is represented by the following reaction formula:

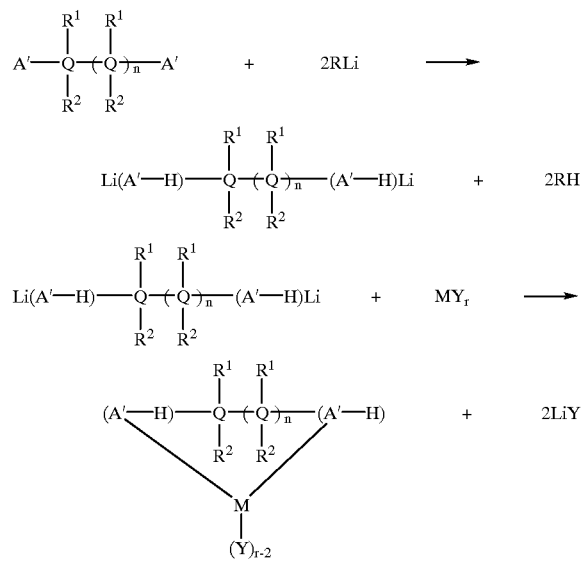

In the above reaction formula, Q, n, $R^1$ and $R^2$ have the same definitions or meanings as described above; A' is a cyclopentadienyl group which may have a condensed ring and/or a substituent group, and two A's are the same or different; (A'-H) is a group formed by eliminating one hydrogen atom from A'; M is a transition metal belonging to 3- to 6-Groups; Y is a halogen atom; and R is a $C_1$ to $C_6$ alkyl group or an aryl group and may include, for example, methyl, n-butyl, sec-butyl, tert-butyl, phenyl or the like; r represents an integer of 3 when M is a 3-Group transition metal, an integer of 4 when M is a 4-Group transition metal, and an integer of 5 when M is a 5-Group transition metal.

Also, as described in European Patent No. 669,340, the transition metal complex can be produced by the method which comprises reacting a dicyclopentadienyl silicon or germanium compound with dibutyl magnesium, and then reacting the reaction product with trialkyl tin and then with the transition metal compound. Further, as described in Japanese Patent Application Laid-Open (KOKAI) No. 8-259582(1996), the transition metal complex can be produced by the method which comprises forming a dianion of the dicyclopentadienyl silicon or germanium compound, and then reacting the dianion with a germanium or tin compound and then with the transition metal compound.

Furthermore, as described in the specification of U.S. Pat. No. 5,495,035, the transition metal complex can be produced by the method of reacting a dicyclopentadienyl silicon compound or a dicyclopentadienyl germanium compound with a transition metal amide compound.

Typical examples of zirconium complexes obtained by the above-mentioned methods may include the below-enumerated compounds. Incidentally, although the below-exemplified transition metal complexes are expressed only by their chemical names, it should be understood that these complexes involve all stereoisomers thereof, if any. In addition, for clear understanding of nomenclatures of these transition metal complexes, the structural formula of the transition metal complex described in (21) hereinafter, is first shown below.

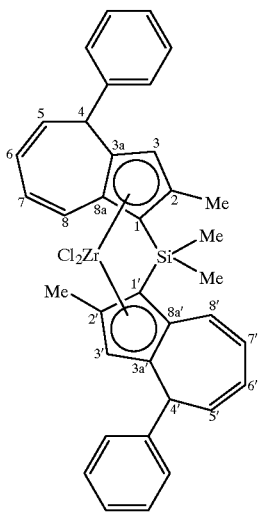

(1) dichloro[1,1'-dimethylsilylene bis(indenyl)] zirconium
(2) dichloro[1,1'-(methyl)(phenyl)silylene bis(indenyl)] zirconium
(3) dichloro[1,1'-diphenylsilylene bis(indenyl)] zirconium
(4) dichloro[1,1'-(1-silacyclopentane-1,1-diyl) bis(indenyl)] zirconium
(5) dichloro[1,1'-(1-sila-2,3,4,5-tetramethyl cyclopentadiene-1,1-diyl) bis(indenyl)] zirconium
(6) dichloro[1,1'-dimethylsilylene bis(2-methyl indenyl)] zirconlium
(7) dichloro[1,1-dimethylsilylene bis(2-methyl-4-phenyl indenyl)] zirconium
(8) dichloro[1,1'-dimethylsilylene bis(2-methyl-4-indolyl indenyl)] zirconium
(9) dichloro[1,1-dimethylsilylene bis(2-ethyl-4-phenyl indenyl)] zirconium
(10) dichloro[1,1'-dimethylsilylene bis(2-methyl-4,5'-benzindenyl)] zirconium
(11) dichloro[1,1'-dimethylsilylene bis(2,4,7-trimethyl indenyl)] zirconium
(12) dichloro[1,1'-dimethylsilylene bis(2-methyl-4-naphthyl indenyl)] zirconium
(13) dichloro[1,1'-dimethylsilylene bis(2-n-propyl-4-phenanthryl indenyl)] zirconium
(14) dichloro[1,1'-dimethylsilylene bis(cyclopentadienyl)] zirconium
(15) dichloro[1,1'-dimethylsilylene bis(2,3,5-trimethyl cyclopentadienyl)] zirconium
(16) dichloro[9,9'-dimethylsilylene bis(fluorenyl)] zirconium
(17) dichloro[1,9-dimethylsilylene (cyclopentadienyl)(fluorenyl)] zirconium
(18) dichloro[1,1'-dimethylsilylene (3-t-butyl cyclopentadienyl)(3-t-butyl indenyl)] zirconium
(19) dichloro[1,1'-dimethylsilylene (2,3,5-trimethyl cyclopentadienyl)(2-methyl-4-phenyl indenyl)] zirconium
(20) dichloro[1,1'-dimethylsilylene (2-methyl indenyl)(2-methyl-4-phenyl indenyl)] zirconium
(21) dichloro[1,1'-dimethylsilylene bis(2-methyl-4-phenyl-4H-azulenyl)] zirconium
(22) dichloro[1,1'-dimethylsilylene bis(2-ethyl-4-naphthyl-4H-azulenyl)] zirconium
(23) dichloro[1,1'-dimethylsilylene bis(2-i-propyl-4-phenyl-4H-azulenyl)] zirconium
(24) dichloro[1,1'-dimethylsilylene bis(2-benzyl-4-phenyl-7-i-propyl-4H-azulenyl)] zirconium
(25) dichloro{1,1'-dimethylsilylene bis[2-methyl-4-(4-chlorophenyl)-4H-azulenyl]} zirconium
(26) dichloro{1,1'-dimethylsilylene bis[2-methyl-4-(3-trifluoromethylphenyl)-4H-azulenyl]} zirconium
(27) dichloro{1,1'-dimethylsilylene bis[2-methyl-4-(2-fluorophenyl)-4H-azulenyl]} zirconium
(28) dichloro{1,1'-dimethylsilylene [2-methyl-4-(4-t-butylphenyl)-4H-azulenyl]} zirconium
(29) dichloro(1,1'-dimethylsilylene [2-methyl-4-(4-methoxyphenyl)-4H-azulenyl]) zirconium
(30) dichloro(1,1'-dimethylsilylene [2-methyl-4-(4-dimethylaminophenyl)-4H-azulenyl]) zirconium
(31) dichloro[1,1'-dimethylsilylene (2-methyl-4-phenyl-4H-azulenyl)(2,3,5-trimethyl cyclopentadienyl)] zirconium
(32) dichloro[1,1'-dimethylsilylene (2-methyl-4-phenyl-4H-azulenyl)(2-methyl-4-phenyl indenyl)] zirconium
(33) dichloro[1,1'-(4-chlorophenyl)(methyl)silylene bis(2-methyl-4-phenyl-4H-azulenyl)] zirconium
(34) dichloro[1,1'-(4-fluorophenyl)(methyl)silylene bis(2-methyl-4-phenyl-4H-azulenyl)] zirconium
(35) dichloro[1,1'-(chloromethyl)(methyl)silylene bis(2-methyl-4-phenyl-4H-azulenyl)] zirconium In addition, there may be exemplified compounds having such a chemical formula that a silicon atom occupying the Q site of the above general formula (VI) is replaced with a germanium atom. Further, there may be exemplified compounds having such a chemical formula that zirconium (Zr) occupying the M site of the above general formula (VI) is replaced with Ti, Hf, Ta, Nb, V, W, Mo, Sc, Y, La, Sm, Ac, Th or the like. Further, there may be exemplified compounds having such a chemical formula that one of chlorine atoms occupying the Y site of the above general formula (VI) is replaced with a fluorine atom, a bromine atom, an iodine atom, a dimethylamino group, a diethylamino group or the like. Also, according to known methods, the above Y may be converted into a hydrogen atom, a methyl group, a phenyl group, a fluorophenyl group, a benzyl group, a methoxy group or the like. Furthermore, as described in Japanese Patent Application Laid-Open (KOKAI) No. 8-59724 (1996), the above-mentioned compounds may be converted into those having such a structure that a part or whole of unsaturated bonds existing at a condensed ring portion of the cyclopentadienyl group which constitutes the (A'-H) portion of the above general formula (VI) and may have a condensed cyclic hydrocarbon group thereon, are hydrogenated.

Next, the process for producing a catalyst for the polymerization of α-olefin according to the present invention, is explained. As the catalyst for the polymerization of α-olefin according to the present invention, there may be exemplified the following catalysts (1) and (2). Both of the catalysts contain the above-mentioned transition metal complex of the present invention as an essential component (A).

(1) Catalyst for the polymerization of α-olefin which contains the following essential components (A) and (B), and optional component (C).

Component (A): Transition metal complex;
Component (B): Aluminum oxy compound, ionic compound capable of reacting with the component (A) so as to convert the component (A) into a cation, or Lewis acid; and
Component (C): carrier composed of fine particles.

(2) Catalyst for the polymerization of α-olefin which contains the following essential components (A) and (D), and optional component (E).

Component (A): Transition metal complex;
Component (D): Ion-exchangeable layer compound except for silicates, or inorganic silicates; and Component (E): Organic aluminum compound.

First, the catalyst (1) for the polymerization of α-olefin is explained. This catalyst contains an aluminum oxy compound, an ionic compound capable of reacting with the component (A) so as to convert the component (A) into a cation, or a Lewis acid as the essential component (B) in addition to the transition metal complex (A), and further contains a carrier composed of fine particles as the optional component (C). Incidentally, certain kinds of the above-described Lewis acids can also be regarded as the ionic compounds capable of reacting with the component (A) so as to convert the component (A) into a cation. Accordingly, it should be understood that those compounds belonging to both the above Lewis acid and ionic compound can be used as any one thereof.

As the afore-mentioned aluminumoxy compounds, there can be exemplified those compounds represented by the following general formulae (VIII), (IX) and (X):

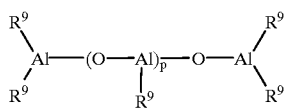
(VI)

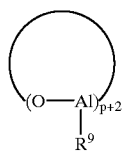
(VII)

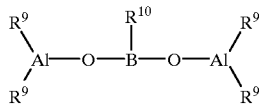
(VIII)

In the afore-mentioned general formulae (VI), (VII) and (VIII), $R^9$ is a hydrogen atom or a hydrocarbon group having preferably 1 to 10 carbon atoms, more preferably 1 to 6 carbon atoms, providing that when a plurality of the $R^9$ are present in the same molecule, these $R^9$ may be the same or different; and p is an integer of 0 to 40, preferably 2 to 30.

The compounds represented by the general formulae (VI) and (VII) are also called "alumoxane", and can be obtained by reacting at least one trialkylaluminum with water. Specific examples of the compounds represented by the general formulae (VI) and (VII) may include (i) compounds obtained by reacting one kind of trialkylaluminum with water, such as methylalumoxane, ethylalumoxane, propylalumoxane, butylalumoxane or isobutylalumoxane, (ii) compounds obtained by reacting two kinds of trialkylaluminum with water, such as methylethylalumoxane, methylbutylalumoxane or methylisobutylalumoxane, or the like. Among them, methylalumoxane and methylisobutylalumoxane are preferred.

The afore-mentioned alumoxanes can be used in combination within each group or between a plurality of groups. The alumoxanes can be prepared under various known conditions. Specifically, the following methods can be used for the production of these alumoxanes:

(a) Method of directly reacting trialkylaluminum with water in the presence of an appropriate organic solvent such as toluene, benzene or ether;
(b) Method of reacting trialkylaluminum with a salt containing crystallization water, e.g., a hydrate of copper sulfate or aluminum sulfate;
(c) Method of reacting trialkylaluminum with a water content impregnated in silica gel or the like;
(d) Method of mixing trimethylaluminum and triisobutylaluminum together, and then directly reacting the mixed trialkylaluminums with water in the presence of an appropriate organic solvent such as toluene, benzene or ether;
(e) Method of mixing trimethylaluminum and triisobutylaluminum together, and then reacting the mixed trialkylaluminums with a salt containing crystallization water, e.g., a hydrate of copper sulfate or aluminum sulfate while heating;
(f) Method of impregnating water into silica gel or the like, and treating the water-impregnated silica gel, etc., with triisobutylaluminuin and then with trimethylaluminum;
(g) Method of preparing methylalumoxane and isobutylalumoxane by a known method, and then mixing these two components together at a predetermined ratio to be reacted with each other while heating; and
(h) Method of adding a salt containing crystallization water such as copper sulfate pentahydrate and trimethylaluminum into an aromatic hydrocarbon solvent such as benzene or toluene and reacting these components with each other at a temperature of about −40° C. to about 40° C.

The molar ratio of water used to the trimethylaluminum is usually in the range of 0.5 to 1.5. Methylalumoxane prepared by the afore-mentioned methods is a linear or cyclic organoaluminum polymer.

The compounds represented by the general formula (VIII) can be obtained by reacting at least one trialkylaluminum with alkyl boric acid represented by the following general formula (IX) at a molar ratio of 10:1 to 1:1.

$$R^{10}B(OH)_2 \qquad (IX)$$

wherein $R^{10}$ is a hydrocarbon group or a halogenated hydrocarbon group both having 1 to 10 carbon atoms, preferably 1 to 6 carbon atoms.

Specific examples of the compounds represented by the general formula (IX) may include the following reaction products:

(a) Reaction products obtained by reacting trimethylaluminum with methylboric acid at a molar ratio of 2:1;
(b) Reaction products obtained by reacting triisobutylaluminum with methylboric acid at a molar ratio of 2:1;
(c) Reaction products obtained by reacting trimethylaluminum, triisobutylaluminum and methylboric acid with each other at a molar ratio of 1:1:1;
(d) Reaction products obtained by reacting trimethylaluminum with ethylboric acid at a molar ratio of 2:1; and
(e) Reaction products obtained by reacting triethylaluminum with butylboric acid at a molar ratio of 2:1.

In addition, as the ionic compounds capable of reacting with the component (A) to convert the component (A) into a cation, there can be exemplified those compounds represented by the general formula (X):

$$[K]e^+[Z]e^- \qquad (X)$$

In the general formula (X), K represents a cationic component. Examples of the cations may include carbonium cation, tropylium cation, ammonium cation, oxonium cation, sulfonium cation, phosphonium cation or the like. Further, metal cations which tend to be reduced per se, cations of organic metals or the like can also be used.

Specific examples of the afore-mentioned cations may include triphenyl carbonium, diphenyl carbonium, cyclohepta trienium, indenium, triethylammonium, tripropylammonium, tributylammonium, N, N-dimethylammonium, dipropylammonium, dicyclohexylammonium, triphenylphosphonium, trimethylphosphonium, tris(dimethylphenyl)phosphonium, tris(methylphenyl)phosphonium, triphenylsulfonium, triphenyloxonium, triethyloxonium, pyrylium, silver ion, gold ion, platinum ion, copper ion, palladium ion, mercury ion, ferrocenium ion or the like.

In the general formula (X), Z represents an ionic anion component (generally a non-coordinated component), which constitutes a counter anion against the cation produced by the conversion of the component (A). As the anion Z, there can be exemplified anions of organic boron compounds, anions of organoaluminum compounds, anions of organogallium compounds, anions of organophosphorus compounds, anions of organoarsenic compounds, anions of organoanthimony compounds or the like. Specific examples of these organic compounds are as follows.

(a) tetraphenylboron, tetrakis(3,4,5-trifluorophenyl)boron, tetrakis{3,5-bis(trifluoromethyl)phenyl}boron, tetrakis{3,5 -di(t-butyl)phenyl}boron, tetrakis (pentafluorophenyl)boron, or the like;
(b) tetraphenylaluminum, tetrakis(3,4,5-trifluorophenyl) aluminum, tetrakis{3,5-bis(trifluoromethyl) phenyl}aluminum, tetrakis(3,5-di(t-butyl)phenyl) aluminum, tetrakis(pentafluorophenyl)aluminum, or the like;
(c) tetraphenylgallium, tetrakis(3,4,5-trifluorophenyl}gallium, tetrakis{3,5-bis(trifluoromethyl) phenyl)gallium, tetrakis(3,5-di(t-butyl)phenyl)gallium, tetrakis(pentafluoro)phenylgallium, or the like;
(d) tetraphenyl phosphorus, tetrakis(pentafluorophenyl) phosphorus, or the like;
(e) tetraphenyl arsenic, tetrakis(pentafluorophenyl) arsenic, or the like;
(f) tetraphenyl antimony, tetrakis(pentafluorophenyl) antimony, or the like; and
(g) decaborate, undecaborate, carbadodecaborate, decachlorodecaborate, or the like.

Further, as the Lewis acids, especially those capable of converting the component (A) into a cation, there can be exemplified various organoboron compounds, halogenated metal compounds, solid acids or the like. Specific examples of these Lewis acids are as follows:

(a) organoboron compounds such as triphenylboron, tris(3, 5-difluorophenyl)boron or tris(pentafluorophenyl)boron;
(b) halogenated metal compounds such as aluminum chloride, aluminum bromide, aluminum iodide, magnesium chloride, magnesium bromide, magnesium iodide, magnesium chloride bromide, magnesium chloride iodide, magnesium bromide iodide, magnesium chloride hydride, magnesium chloride hydroxide, magnesium bromide hydroxide, magnesium chloride alkoxide or magnesium bromide alkoxide; and
(c) solid acids such as alumina or silica-alumina.

In the catalyst (1) for polymerization of α-olefin, the fine particle carrier as the optional component (C) may be composed of an inorganic or organic compound, and in the form of granules or particles having a particle diameter of usually 5 μm to 5 mm, preferably 10 μm to 2 mm. As the afore-mentioned inorganic carrier, there can be exemplified oxides such as $SiO_2$, $Al_2O_3$, MgO, ZrO, $TiO_2$, $B_2O_3$ or ZnO; composite oxides such as $SiO_2$—MgO, $SiO_2$—$Al_2O_3$, $SiO_2$—$TiO_2$, $SiO_2$—$Cr_2O_3$ or $SiO_2$—$Al_2O_3$—MgO; or the like.

As the afore-mentioned organic carrier, there can be exemplified fine particles of porous polymers, for example, polymers or copolymers of α-olefins having 2 to 14 carbon atoms such as ethylene, propylene, 1-butene or 4-methyl-1-pentene; polymers or copolymers of aromatic unsaturated hydrocarbons such as styrene or divinylbenzene; or the like. These organic carriers have a specific surface area of usually 20 to 1,000 $m^2/g$, preferably 50 to 700 $m^2/g$, and a pore volume of usually not less than 0.1 $cm^3/g$, preferably not less than 0.3 $cm^3/g$, more preferably not less than 0.8 $cm^3/g$.

The catalyst (1) for polymerization of α-olefin may contain, as other optional components than the fine particle carrier, for example, protic compounds such as $H_2O$, methanol, ethanol or butanol; electron donative compounds such as ethers, esters or amines; alkoxy-containing compounds such as phenylborate, dimethylmethoxyaluminum, phenylphosphite, tetraethoxysilane or diphenyldimethoxysilane; or the like.

As still further optional components other than the afore-mentioned compounds, there can be exemplified tri lower-alkylaluminums such as trimethylaluminum, triethylaluminum or triisobutylaluminum; halogen-containing alkylaluminums such as diethylaluminum chloride, diisobutylaluminum chloride or methylaluminum sesqui-chloride; alkylaluminum hydrides such as diethylaluminum hydride; alkoxy-containing alkylaluminums such as diethylaluminum ethoxide or dimethylaluminum butoxide; aryloxy-containing alkylaluminums such as diethylaluminum phenoxide; or the like.

In the catalyst (1) for polymerization of α-olefin, the aluminum-oxy compound, the ionic compound capable of reacting with the component (A) to convert the component (A) into a cation, and the Lewis acid as the component (B) are used singly or in the form of a mixture of any two or more thereof in combination. Incidentally, it is preferred that as the still further optional components, one or more kinds of the afore-mentioned lower-alkylaluminum, halogen-containing alkylaluminum, alkylaluminum hydride, alkoxy-containing alkylaluminum or aryloxy-containing alkylaluminum are contained in the catalyst (1) for polymerization of α-olefin, together with the aluminum-oxy compound, the ionic compound or the Lewis acid.

The catalyst (1) for polymerization of α-olefin may be prepared by bringing the components (A) and (B) into contact with each other inside or outside of a polymerization vessel and in the presence or absence of a monomer to be polymerized. In this case, the components (A) and (B), and if required, the component (C), etc., may be introduced separately into the polymerization vessel. Alternatively, the components (A) and (B) may be introduced into the polymerization vessel after both the components have been preliminarily brought into contact with each other. Further, after the components (A) and (B) are mixed together and impregnated into the component (C), the mixture may be introduced into the polymerization vessel.

The contact between the respective components can be conducted in an atmosphere containing an inert gas such as nitrogen or in the presence of an inert hydrocarbon solvent such as pentane, hexane, heptane, toluene or xylene. In addition, the contact can be conducted at a temperature of from −20° C. to a boiling point of the solvent used, preferably from room temperature to the boiling point of the solvent used. The thus-produced catalyst may be used as it is without washing, or may be used after washing. Further, the obtained catalyst may be used in combination with additional components, if required.

Also, when the components (A), (B) and (C) are preliminarily brought into contact with each other, the contact can be performed in the presence of the monomer to be polymerized, i.e., α-olefin to partially polymerize the α-olefin (so-called pre-polymerization). More specifically, before the polymerization, the α-olefin such as ethylene, propylene, 1-butene, 1-hexene, 1-octene, 4-methyl-1-pentene, 3-methyl-1-butene, vinylcycloalkanes or styrene is pre-polymerized and washed, if required. The thus-produced pre-polymerization product can be used as a catalyst. In this case, it is preferred that the pre-polymerization is conducted in the presence of an inert solvent under such a moderate reaction condition that the polymer is produced in an amount of usually 0.01 to 1,000 g, preferably 0.1 to 100 g based on one gram of the solid catalyst.

The amounts of the components (A) and (B) used are optional. For example, in the case of solution polymerization, the amount of the component (A) used is usually in the range of $10^{-7}$ to $10^2$ mmol/liter (calculated as the transition metal) preferably $10^{-4}$ to 1 mmol/liter. In the case where the aluminum-oxy compound is used as the component (B), the molar ratio of Al to the transition metal is usually in the range of 10 to $10^5$, preferably 100 to $2\times10^4$, more preferably 100 to 104. On the other hand, in the case where the ionic compound or the Lewis acid is used as the component (B), the molar ratio of the ionic compound or the Lewis acid to the transition metal is usually in the range of 0.1 to 1,000, preferably 0.5 to 100, more preferably 1 to 50.

Next, the catalyst (2) for polymerization of α-olefin according to the first aspect of the present invention is explained below. The catalyst (2) comprises, as essential components, the afore-mentioned transition metal compound (component A) and the specific ion exchangeable layer compound or the inorganic silicate (component (D)), and as an optional component, the organoaluminum compound (component (E)).

First, as the component D, the inorganic silicate or the ion exchangeable layer compound except for silicate (hereinafter referred to merely as "ion exchangeable layer compound") is described in detail below.

As the afore-mentioned ion exchangeable layer compounds as the component (D), there can be exemplified ionic crystalline compounds of a hexagonal closest packing type, an antimony type, a $CdCl_2$ type or a $CdI_2$ type, which have a layer crystal structure. Specific examples of the ion exchangeable layer compounds may include crystalline acid salts of polyvalent metals such as α-$Zr(HAsO_4)_2 \cdot H_2O$, α-$Zr(HPO_4)_2$, α-$Zr(KPO_4)_2 \cdot 3H_2O$, α-$Ti(HPO_4)_2$, α-$Ti(HAsO_4)_2 \cdot H_2O$, α-$Sn(HPO_4)_2 \cdot H_2O$, γ-$Zr(HPO_4)_2$, γ-$Ti(HPO_4)_2$ or γ-$Ti(NH_4PO_4)_2 \cdot H_2O$.

The afore-mentioned ion exchangeable layer compounds may be treated with salts and/or acids, if required. The ion exchangeable layer compounds except for silicates which are treated with neither salts nor acids, have such a crystal structure that layers formed by ionic bond or the like are overlapped in parallel to one another with a weak bonding force therebetween and, therefore, the layers contain ions exchangeable with each other.

As the afore-mentioned inorganic silicates as the component (D), there can be exemplified clays, clay minerals, zeolite, diatomaceous earth or the like. These inorganic silicates may be either synthesized products or naturally outputted minerals. Specific examples of clays or clay minerals may include allophane group clays or clay minerals such as allophane; kaolin group clays or clay minerals such as dickite, nacrite, kaolinite or anauxite, halloysite group clays or clay minerals such as meta-halloysite or halloysite; serpentine group clays or clay minerals such as chrysotile, lizardite or antigorite; smectite group clays or clay minerals such as montmorillonite, sauconite, beidellite, nontronite, saponite or hectorite; vermiculite minerals such as vermiculite; mica minerals such as illite, sericite or glauconite; attapulgite; sepiolite; palygorskite; bentonite; gnarl clay; gairome clay hisingerite; pyrophyllite; chlorite groups; or the like. These inorganic silicates may be in the form of mixed layers thereof. In addition, as the synthetic inorganic silicates, there can be exemplified synthetic mica, synthetic hectorite, synthetic saponite, synthetic taeniolite or the like.

Among the afore-mentioned inorganic silicates, kaolin group clays or clay minerals, halloysite group clays or clay minerals, serpentine group clays or clay minerals, smectite-group clays or clay minerals, vermiculite minerals, mica minerals, synthetic mica, synthetic hectorite, synthetic saponite or synthetic taeniolite are preferred, and especially preferred inorganic silicates are smectite, vermiculite minerals, synthetic mica, synthetic hectorite, synthetic saponite and synthetic taeniolite. These inorganic silicates may be used in untreated state as they are, or may be used after subjected to treatments such as crushing by a ball mill, screening or the like. Further, these inorganic silicates may be used singly or in the form of a mixture of any two or more thereof.

The afore-mentioned ion exchangeable layer compounds except for silicates and the inorganic silicates as the component (D) can be treated with salts and/or acids to control an acid strength of these solid compounds. Further, when these compounds are treated with salts, ion composites, molecule composites or organic derivatives are formed, so that it becomes possible to appropriately change the surface area and interlayer distance thereof. Specifically, exchangeable ions existing between the respective layers can be replaced with other bulkier ions by the aid of ion exchanging properties of these compounds, thereby obtaining a layer substance having an increased interlayer distance.

If these compounds are not pre-treated as described above, it is preferred that metal cations contained therein are ion-exchanged with cations dissociated from the below-mentioned salts and/or acids.

The salts used for the afore-mentioned ion exchange, may be compounds comprising a cation which contains at least one atom selected from the group consisting of Group 1–14 atoms, preferably compounds comprising a cation which contains at least one atom selected from the group consisting of Group 1–14 atoms and at least one anion derived from an atom or atomic group selected from the group consisting of halogen atoms, inorganic acids and organic acids, more preferably compounds comprising a cation which contains at least one atom selected from the group consisting of Group 2–14 atoms and at least one anion selected from the group consisting of Cl, Br, I, F, $PO_4$, $SO_4$, $NO_3$, $CO_3$, $C_2O_4$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH and $OOCCH_2CH_3$. These salts may be used singly or in the form of a mixture of any two or more thereof in combination.

The acids used for the aforementioned ion exchange, may be selected from hydrochloric acid, sulfuric acid, nitric acid, acetic acid and oxalic acid. These acids may be used singly or in the form of a mixture of any two or more thereof. The salt treatment can be used in combination with the acid treatment. As methods in which the salt treatment and the acid treatment are used in combination, there can be exemplified a method of conducting the acid treatment after the salt treatment, a method of conducting the salt treatment after the acid treatment, a method of conducting the salt and acid treatments simultaneously, and a method of conducting the salt and acid treatments simultaneously after the salt treatment. Incidentally, the acid treatment has such effects, afore-mentioned ion exchange that impurities can be removed from the surface of the component (D), and that a part of cations contained in the crystal structure such as Al, Fe, Mg or Li can be eluted therefrom.

The treating conditions used for the salt or acid treatment are not particularly restricted. However, it is preferable that the concentration of the salt or acid is usually in the range of 0.1 to 30% by weight; the treating temperature is usually from room temperature to a boiling point of solvent used; and the treating time is usually from 5 minutes to 24 hours, such that at least a part of the compound to be treated is solved out. Further, the salts and the acids are usually used in the form of an aqueous solution.

In the afore-mentioned salt and/or acid treatments, the component (D) may be pulverized or granulated before, during or after the salt and/or acid treatments to control the shape thereof. In addition, other chemical treatments such as alkali treatment or treatments by organic substances may be used in combination. The thus-prepared component (D) has preferably a pore volume of usually not less than 0.1 cc/g, more preferably 0.3 to 5 cc/g, when measured with respect to pores having a radius of not less than 20 Å by a mercury-penetrating method. Such a component (D) generally contains an absorbed water or an interlayer water. Here, the absorbed water means water absorbed on a surface or a crystal fracture face of the ion exchangeable layer compound or the inorganic silicate, and the interlayer water means water existing between the layers.

In accordance with the present invention, it is preferred that the component (D) is used after removal of the afore-mentioned absorbed water or interlayer water. The methods for removing the water, are nor particularly restricted, but there can be used dehydrating methods such as heating, heating in the presence of a flowing gas, heating under a reduced pressure, azeotropy with an organic solvent, or the like. The heating may be conducted at such a temperature that no absorbed water and interlayer water exists in the component (D). The heating temperature is usually not less than 100° C., preferably not less than 150° C. However, the use of such a high temperature which causes destruction of the crystal structure should be avoided. The heating time is usually not less than 0.5 hour, preferably not less than one hour. The weight loss of the thus-treated component (D) is preferably not more than 3% by weight, when the suction is conducted at a temperature of 200° C. under a pressure of 1 mmHg for 2 hours. In accordance with the present invention, in the case where the component (D) whose weight loss is adjusted to not more than 3% by weight based on the weight of the component (D) is used, it is preferred that the weight loss of the component (B) is also maintained when the component (D) is brought into contact with the essential component (A) and the below-mentioned optional component (E).

Next, the organoaluminum compound (component (E)) is explained in detail below. As the component (E), there can be preferably used organoaluminum compounds represented by the general formula (XI):

$$AlR_aP_{3-a} \quad (XI)$$

wherein R is a hydrocarbon group having 1 to 20 carbon atoms; P is a hydrogen atom, a halogen atom, an alkoxy group or a siloxy group; and "a" is a number satisfying 0<a 3.

Specific examples of the organoaluminum compounds represented by the afore-mentioned general formula (XI) may include trialkylaluminums such as trimethylaluminum, triethylaluminum, tripropylaluminum or triisobutylaluminum, halogen-containing or alkoxy-containing alkylaluminums such as diethylaluminum monochloride or diethylaluminum monomethoxide, or the like. Among them, trialkylaluminums can be preferably used. Further, in the case of the catalyst (2) for polymerization of α-olefin according to the first aspect of the present invention, aluminoxanes such as methylaluminoxane or the like can also be used as the component (E).

The catalyst (2) for polymerization of α-olefin can be prepared by bringing the essential components (A) and (B) and the optional component (E) in contact with each other. The contacting method is not particularly restricted, but the following methods (i) to (v) can be exemplified. Incidentally, the contact between these components may be performed not only upon the production of the catalyst but also upon pre-polymerization or polymerization of the olefins.

(i) Method of bringing the components (A) and (D) into contact with each other;

(ii) Method of bringing the components (A) and (D) into contact with each other and then adding the component (E) to the mixture;

(iii) Method of bringing the components (A) and (E) into contact with each other and then adding the component (D) to the mixture;

(iv) Method of bringing the components (D) and (E) into contact with each other and then adding the component (A) to the mixture; and (v) Method of bringing the components (A), (D) and (E) into contact with each other at the same time.

When or after the respective components are brought into contact with each other, polymers such as polyethylene or polypropylene or solid components of inorganic oxides such as silica or alumina may co-exist therein or may be contacted therewith.

In addition, the contact between the respective components can be conducted in an atmosphere of an inert gas such as nitrogen or in the presence of an inert hydrocarbon solvent such as pentane, hexane, heptane, toluene or xylene. Further, the contact is preferably conducted at a temperature of from −20° C. to a boiling point of the solvent used, more preferably from room temperature to the boiling point of the solvent used.

The amount of the component (A) used is usually in the range of $10^{-4}$ to 10 mmol, preferably $10^{-3}$ to 5 mmol based on one gram of the component (D). The amount of the component (E) used is usually in the range of 0.01 to $10^4$ mmol, preferably 0.1 to 100 mmol based on one gram of the component (D). In addition, the atomic ratio of the transition metal contained in the component (A) to aluminum contained in the component (E) is usually in the range of 1/0.01 to 1/106, preferably 1/0.1 to $1/10^5$. The thus-prepared catalyst may be used as it is without washing, or may be used after washing. Further, the catalyst can be used in combination with a further component (E) which is composed of similar compounds to the component (E), if required. That is, when the components (A) and/or (D) and the component (E) are used to prepare the catalyst, the further component (E) may be added to a reaction system separately from that the component (E) used for the preparation of the catalyst. In this case, the amount of the further added component (E) can be selected such that the atomic ratio of the transition metal contained in the component (A) to aluminum contained in the further added component (E) is 1/0 to $1/10^4$.

Next, the method for producing an α-olefin polymer according to the present invention, is explained in detail below. In accordance with the present invention, the afore-mentioned catalyst and α-olefin are brought into contact with each other to polymerize or copolymerize the α-olefin. The catalyst for polymerization of α-olefin according to the present invention can be applied to not only a solution polymerization using a solvent, but also a liquid-phase non-solvent polymerization using substantially no solvent, a gas-phase polymerization or a melt polymerization. These polymerizations can be conducted either in a continuous manner or in a batch manner.

As the solvents used for the solution polymerization, there can be exemplified inert saturated aliphatic or aromatic hydrocarbons such as hexane, heptane, pentane, cyclohexane, benzene or toluene. These solvents can be used singly or in the form of a mixture of any two or more thereof. The polymerization temperature is usually in the range of −78° C. to 250° C., preferably −20° C. to 100° C. The olefin pressure in the reaction system is not particularly restricted, but preferably from ordinary pressure to 2,000 kgf/cm$^2$G (Geuge), more preferably from ordinary pressure to 50 kgf/cm$^2$G. Further, the molecular weight of the resultant α-olefin polymer can be controlled by known methods such as appropriate selection of reaction temperature and reaction pressure used or introduction of hydrogen.

As the raw α-olefins, there can be used α-olefins having usually 2 to 20 carbon atoms, preferably 2 to 10 carbon atoms. Specific examples of the α-olefins may include ethylene, propylene, 1-butene, 4-methyl-1-pentene, 1-hexene, 1-octene, 1-decene, 1-dodecene, 1-tetradecene, 1-hexadecene, 1-octadecene, 1-eicosene or the like. The catalyst according to the present invention can be preferably applied to stereoregulated polymerization of α-olefins having 3 to 10 carbon atoms, especially to the polymerization of propylene.

Further, the catalyst according to the present invention can be applied to not only homopolymerization or copolymerization of the afore-mentioned α-olefins, but also copolymerization of the x-olefins with the other monomers. As the other monomers copolymerizable with the α-olefins, there can be exemplified conjugated dienes or non-conjugated dienes such as butadiene, 1,4-hexadiene, 7-methyl-1,6-octadiene, 1,8-nonadiene or 1,9-decadiene; cyclic olefins such as cyclopropene, cyclobutene, cyclopentene, norbornene or dicyclopentadiene; or the like. The polymerization or copolymerization of the α-olefins can be performed in multiple stages whose reaction conditions are different from each other, i.e., in a manner of so-called multi-step polymerization, for example, block copolymerization comprising pre-polymerization of propylene and copolymerization of ethylene with the polypropyrene prepared by the said pre-polymerization.

BEST MODE FOR CARRYING OUT THE INVENTION

The present invention is described in more detail below by way of examples, but these examples are not intended to limit the scope of the present invention. Incidentally, in the following examples, all the catalyst preparation processes and polymerization processes were conducted in a purified nitrogen atmosphere. In addition, solvents were dehydrated with MS-4A and then deaerated by bubbling with purified nitrogen before they were used for these processes. Further, the activity of each solid catalyst component per unit weight thereof is referred to as "catalytic activity" and indicated by a unit of "g-polymer/g-solid catalyst component", whereas the activity of each complex component per unit weight thereof is referred to as "complex activity" and indicated by a unit of "g-polymer/g-complex component".

(1) Measurement of Melt Flow Rate (MFR):

Six grams of an acetone solution containing 0.6% by weight of a thermal stabilizer (BHT) was added to 6 g of the obtained polymer. After drying, the polymer was charged into a melt indexer (230° C.) and allowed to stand for 5 minutes under a load of 2.16 Kg. Thereafter, the polymer was extruded to measure the amount of the extruded polymer. Based on the thus-measured amount of the extruded polymer, the amount per 10 minutes was calculated and used as a value of MFR.

(2) Measurement of Molecular Weight Distribution:

The molecular weight distribution of the obtained polymer was determined from the Q-value (Mw/Mn) of weight-average molecular weight (Mw) to number-average molecular weight (Mn) thereof which were measured by gel permeation chromatography (GPC). The measurement of the molecular weights was conducted at 135° C. by a GPC apparatus (150CV type manufactured by Waters), using ortho-dichlorobenzene as a solvent.

(3) Measurement of Melting Point:

Using a differential scanning calorimeter (DSC) manufactured by E. I. du Pont, the melting point was measured during the second-heating after the first-heating from 20° C. to 200° C. at a heating rate of 10° C/min and cooling.

EXAMPLE 1

427 mg of 2-methyl azulene (3 mmol) was dissolved in 6 ml of hexane, and 3 ml of phenyl lithium (cyclohexane-diethyl ether solution: 1M) was added to the obtained solution at 0 to −5° C. using a syringe. Thereafter, the reaction solution was allowed to stand for returning to room temperature, and then stirred for one hour and 15 minutes, thereby precipitating a lithium salt. 1-methyl imidazole was added to the obtained suspension in an amount of 0.1 equivalent (12 µl) based on dimethyl dichlorosilane added subsequently, and the suspension was further stirred for 15 minutes. The suspension was cooled to 0° C., and mixed with 6 ml of tetrahydrofuran (THF) to dissolve the lithium salt therein. Thereafter, the reaction solution was cooled to −70° C. in a dry-ice ethanol bath, and then 0.18 ml (1.5 mmol) of dimethyl dichlorosilane was added to the solution.

The obtained reaction solution was allowed to stand for returning to room temperature (needed 20 minutes), and further stirred for 40 minutes. The thus obtained reaction solution was mixed with 10 ml of a saturated aqueous ammonium chloride solution, and then washed with water two times. Thereafter, the obtained organic phase was mixed with hexane to prepare 50 ml of a solution. 0.1 ml of the solution was diluted by adding 0.9 ml of acetonitrile thereto such that the concentration thereof was reduced to one-tenth. 5 ul of the dilute solution was sampled and analyzed by a high-performance liquid chromatography.

As a result, it was confirmed that the yield of the aimed bis(2-methyl-4-phenyl-1,4-dihydro-1-azulenyl) dimethylsilane was 86.5%. Further, the reaction product was purified by a silica gel column chromatography, so that bis(2-methyl-4-phenyl-1,4-dihydro-1-azulenyl) dimethylsilane was obtained in the form of an isolated state with a yield of 80.2%.

EXAMPLE 2

The same procedure as defined in Example 1 was conducted except that after dissolving the lithium salt by adding THF to the suspension, the suspension was cooled to 0 to −5° C. As a result, it was confirmed that the yield of the aimed bis(2-methyl-4-phenyl-1,4-dihydro-1-azulenyl) dimethylsilane was 87.2%.

EXAMPLE 3

The same procedure as defined in Example 1 was conducted except that THF was changed to di-i-propyl ether. As a result, it was confirmed that the yield of the aimed bis(2-methyl-4-phenyl-1,4-dihydro-1-azulenyl) dimethylsilane was 85.5%.

EXAMPLE 4

The same procedure as defined in Example 1 was conducted except that 1-methyl imidazole was changed to 18 mg (0.1 equivalent based on dimethyldichloro silane) of 4-dimethylamino pyridine, and THF was changed to di-i-propyl ether. As a result, it was confirmed that the yield of the aimed bis(2-methyl-4-phenyl-1,4-dihydro-1-azulenyl) dimethylsilane was 75.8%.

EXAMPLE 5

The same procedure as defined in Example 2 was conducted except that 1-methyl imidazole was changed to 9 mg (0.05 equivalent based on dimethyldichloro silane) of 4-dimethylamino pyridine, and THF was changed to di-i-propyl ether. As a result, it was confirmed that the yield of the aimed bis(2-methyl-4-phenyl-1,4-dihydro-1-azulenyl) dimethylsilane was 73.0%.

EXAMPLE 6

The same procedure as defined in Example 1 was conducted except that 1-methyl imidazole was changed to 20 mg (0.1 equivalent based on dimethyldichloro silane) of 1-methylbenzimidazole. As a result, it was confirmed that the yield of the aimed bis(2-methyl-4-phenyl-1,4-dihydro-1-azulenyl) dimethylsilane was 68.3%.

EXAMPLE 7

The same procedure as defined in Example 1 was conducted except that 1-methyl imidazole was changed to 10 mg (0.1 equivalent based on dimethyldichloro silane) of 1,2,4-triazole. As a result, it was confirmed that the yield of the aimed bis(2-methyl-4-phenyl-1,4-dihydro-1-azulenyl) dimethylsilane was 66.1%.

EXAMPLE 8

The same procedure as defined in Example 1 was conducted except that 1-methyl imidazole was changed to 11 mg (0.1 equivalent based on dimethyldichloro silane) of tetrazole. As a result, it was confirmed that the yield of the aimed bis(2-methyl-4-phenyl-1,4-dihydro-1-azulenyl) dimethylsilane was 74.1%.

COMPARATIVE EXAMPLE 1

The same procedure as defined in Example 1 was conducted except that 1-methyl imidazole was not added. As a result, it was confirmed that the yield of the aimed bis(2-methyl-4-phenyl-1,4-dihydro-1-azulenyl) dimethylsilane was 31.9%.

COMPARATIVE EXAMPLE 2

The same procedure as defined in Example 1 was conducted except that 1-methyl imidazole was not added, and after dissolving the lithium salt by adding THF to the suspension, the suspension was cooled to 0 to −5° C. As a result, it was confirmed that the yield of the aimed bis(2-methyl-4-phenyl-1,4-dihydro-1-azulenyl) dimethylsilane was 35.8%.

COMPARATIVE EXAMPLE 3

The same procedure as defined in Example 1 was conducted except that 1-methyl imidazole was changed to 23 μl (0.1 equivalent based on dimethyldichloro silane) of N,N',N',N'-tetramethyl ethylene diamine. As a result, it was confirmed that the yield of the aimed bis(2-methyl-4-phenyl-1,4-dihydro-1-azulenyl) dimethylsilane was 27.6%.

COMPARATIVE EXAMPLE 4

The same procedure as defined in Example 1 was conducted except that 1-methyl imidazole was changed to 337 mg (2 equivalents based on dimethyldichloro silane) of 1,4-diazabicyclo[2,2,2]octane which was added to the hexane solution of 2-methyl azulene before adding phenyl lithium to the hexane solution. As a result, it was confirmed that the yield of the aimed bis(2-methyl-4-phenyl-1,4-dihydro-1-azulenyl) dimethylsilane was 14.7%.

COMPARATIVE EXAMPLE 5

The same procedure as defined in Example 1 was conducted except that 1-methyl imidazole was changed to 22 μl (0.1 equivalent based on dimethyldichloro silane) of 1,8-diazabicyclo[5,4,0]-7-undecene. As a result, it was confirmed that the yield of the aimed bis(2-methyl-4-phenyl-1,4-dihydro-1-azulenyl) dimethylsilane was 17.1%.

EXAMPLE 9

71 mg (0.5 mmol) of 2-methyl azulene was dissolved in 0.5 ml of hexane, and 0.5 ml of phenyl lithium (cyclohexane-diethyl ether solution: 1M) was added to the obtained solution at room temperature using a syringe. The solution was stirred at room temperature for 20 minutes, thereby precipitating a lithium salt. Thereafter, 0.4 ml of THF was added to the obtained suspension to dissolve the lithium salt therein. Separately, isoxazole (0.025 mmol) was added to 0.25 ml (0.25 mmol) of a 1M-dimethyldichlorosilane THF solution and dissolved therein. Thereafter, the lithium salt-containing solution was dropped into the thus obtained solution at 0° C., and the mixture was stirred at that temperature for 5 hours. The obtained reaction solution was allowed to stand for returning its temperature to room temperature, and then mixed with 0.5 ml of a saturated aqueous sodium bicarbonate solution. An organic phase was separated from the reaction solution, and extracted with hexane two times. The obtained extract was dried and then evaporated to remove a solvent therefrom, thereby obtaining a brown oil. The obtained oil was analyzed by a high-performance liquid chromatography. A sample to be analyzed was prepared by adding acetonitrile to the oil so as to adjust the concentration of the oil to 1 mg/ml. As a result, it was confirmed that the yield of the aimed bis(2-methyl-4-phenyl-1,4-dihydro-1-azulenyl) dimethylsilane was 50.4%.

EXAMPLE 10

1.5 g of 2-methyl azulene was dissolved in 38 ml of hexane, and 9.8 ml of phenyl lithium (cyclohexane-diethyl ether solution: 1.1M) was added to the obtained solution. The obtained reaction solution was placed in a cooling bath so as to control the temperature thereof to 3 to 5° C., and stirred at 5° C. for 5 minutes. The reaction solution was taken out of the cooling bath, and then stirred for one hour and 20 minutes, thereby precipitating a lithium salt. Thereafter, 38 ml of THF was added to the obtained suspension to dissolve the lithium salt therein. The obtained solution was cooled to −3° C., and then 0.02 ml of 1-methyl imidazole and 0.61 ml of dimethyl germanium dichloride were successively added thereto. The solution was stirred for 20 minutes, and further stirred at room temperature for 3.5 hours. The obtained reaction solution was mixed with a saturated aqueous ammonium chloride solution, and then extracted with hexane. The obtained organic phase was washed with brine, dried with magnesium sulfate, and evaporated under reduced pressure to remove a solvent therefrom. 2.9 g of the obtained concentrated residues were purified by a silica gel column chromatography, thereby obtaining 2.42 g of bis(2-methyl-4-phenyl-1,4-dihydro-1-azulenyl) dimethyl germane. The yield was 85%.

EXAMPLE 11

3.5 g of 2-methyl indene was dissolved in a mixed solvent comprising 12.5 ml of toluene and 1 ml of THF. 8.1 ml of n-butyl lithium (n-hexane solution: 1.66 M) was added to the obtained solution at a temperature of 3 to 5° C. The mixture was stirred at 0° C. for 30 minutes and further at a temperature of 65 to 75° C. for 30 minutes, thereby precipitating a lithium salt. Thereafter, the mixture was cooled again to 0° C., and 38 ml of THF was added to the mixture to dissolve the lithium salt therein. The obtained solution was cooled to −3° C., and then successively mixed with 0.02 ml of 1-methyl imidazole and 0.8 ml of dimethylsilyl dichloride. The obtained mixture was stirred at that temperature for 30 minutes and then at room temperature for 2 hours, and allowed to stand for 12 hours. The obtained reaction solution was mixed with a saturated aqueous ammonium chloride solution, and extracted with diethyl ether. The obtained organic phase was washed with brine, dried with magnesium sulfate, and then evaporated under reduced pressure to remove the solvent therefrom. 2.2 g of the obtained concentrated resides was purified by a silica gel chromatography, thereby obtaining 1.81 g of bis(2-methyl-1-indenyl) dimethylsilane. The yield was 87%.

COMPARATIVE EXAMPLE 6

The same procedure as defined in Example 11 was conducted except that 1-methyl imidazole was not added, and the reaction after the addition of dimethylsilyl dichloride was conducted by stirring the reaction mixture under reflux for 2 hours and then allowing the mixture to stand at room temperature for 60 hours, thereby obtaining bis(2-methyl-1-indenyl) dimethylsilane. The yield was 78%.

EXAMPLE 12

1.0 g of 2-methyl indene was dissolved in 15 ml of diethyl ether. 4.6 ml of n-butyl lithium (n-hexane solution: 1.66 M was added to the obtained solution at a temperature of −2 to 5° C. The mixture was stirred at 0° C. for 30 minutes, thereby precipitating a lithium salt. Thereafter, the mixture was successively mixed with 0.02 ml of 1-methyl imidazole and then with 0.6 ml of (methyl)(phenyl)silyl dichloride. The mixture was stirred for 15 minutes and then at room temperature for one hour. The obtained reaction solution was mixed with a saturated aqueous ammonium chloride solution, and extracted with diethyl ether. The obtained organic phase was washed with brine, dried with magnesium sulfate, and then evaporated under reduced pressure to remove the solvent therefrom. 1.5 g of the obtained concentrated resides was purified by a silica gel chromatography, thereby obtaining 0.73 g of bis(2-methyl-1-indenyl)(methyl)(phenyl) silane. The yield was 50%.

COMPARATIVE EXAMPLE 7

The same procedure as defined in Example 12 was conducted except that 1-methyl imidazole was not added. As a result, it was confirmed that the yield of the aimed bis(2-methyl-1-indenyl)(methyl)(phenyl) silane was 8%.

EXAMPLE 13

(1) Synthesis of dichloro[1,1'-dimethylsilylene bis(2-methyl-4-phenyl-4H-azulenyl)] hafnium (a) Synthesis of Racemic and Meso Mixture:

3.22 g of 2-methyl azulene was dissolved in 30 ml of hexane. 21 ml of a cyclohexane/diethyl ether solution of phenyl lithium (1.0 equivalent) was gradually added to the obtained hexane solution at 0° C. After stirring at room temperature for 1.5 hours, the obtained solution was cooled to 78° C., and then mixed with 30 ml of tetrahydrofuran. The solution was mixed with 45 $\mu$mol of 1-methyl imidazole and 1.37 ml of dimethyl dichlorosilane, allowed to stand for returning to room temperature, and then stirred at room temperature for one hour. Thereafter, the solution was mixed with an aqueous ammonium chloride solution, and separated into aqueous and organic phases. The obtained organic phase was dried with magnesium sulfate and evaporated under a reduced pressure to remove the solvent therefrom, thereby obtaining 5.84 g of bis{1,1'-(2-methyl-4-phenyl-1,4-dihydro azulenyl)} dimethylsilane as a crude product.

The thus obtained bis{1,1'-(2-methyl-4-phenyl-1,4-dihydro azulenyl} dimethylsilane crude product was dissolved in 30 ml of diethyl ether. 14.2 ml of a hexane solution of n-butyl lithium (1.6 mol/liter) was dropped into the obtained solution at −78° C., and the mixture was allowed to stand for gradually returning to room temperature, and stirred for 12 hours at room temperature. The obtained solution was distilled under a reduced pressure to remove the solvent therefrom, and then mixed with 80 ml of a mixed solvent comprising toluene and diethyl ether (40:1). The obtained mixture was mixed with 3.3 g of hafnium tetrachloride at -60° C., allowed to stand for gradually returning to room temperature, and stirred at room temperature for 4 hours. The obtained reaction solution was concentrated under reduced pressure. The obtained solid was washed with toluene, and then extracted with dichloromethane, thereby obtaining 1.74 g of a racemic and meso mixture of dichloro [1,1'-dimethylsilylene bis(2-methyl-4-phenyl-4H-azulenyl)] hafnium.

(b) Purification of Racemic Compound:

1.74 g of the racemic and meso mixture produced by repeating the above reaction, was dissolved in 30 ml of dichloromethane, and introduced into a Pyrex glass container equipped with a 1OOW high-pressure mercury vapor lamp. While stirring, the solution was irradiated with light for 40 minutes under ordinary pressure to enhance a percentage of the racemic compound in the mixture, and then distilled under a reduced pressure to remove dichloromethane therefrom. 10 ml of toluene was added to the obtained yellow solid. The mixture was stirred and then filtered. The filtered-out solid was washed with 8 ml of toluene and 4 ml of hexane, thereby obtaining 917 mg of a racemic compound of dichloro[1,1'-dimethylsilylene bis(2-methyl-4-phenyl-4H-azulenyl)] hafnium.

The chemical shifts of $^1$H-NMR of the obtained racemic compound are as follows.

300 MHz, $C_6D_6$ (ppm) d 0.52 (s, 6H, $SiMe_2$), 2.02 (s, 6H, 2-Me), 5.20 (br s, 2H, 4-H), 5.72-5.95 (m, 6H), 6.04 (s, 2H), 6.75 (d, j=12 Hz, 2H), 7.00-7.2 (m, 6H, arom), 7.53 (d, j=6 Hz, 4H, arom)

The result of mass spectrometry of the racemic compound was "negative CI-MS744 ($M^+C_{36}H_{34}^{35}Cl_2Si^{180}Hf$)".

(2) Polymerization of Protylene:

0.25 mmol (calculated as Al atom) of triisobutyl aluminum (produced by Toso-Akzo Co., Ltd.) was charged into a 1-liter stirring-type autoclave. Separately, 1.12 mg of the racemic compound obtained in the above (1) was diluted with toluene and charged into a catalyst feeder equipped with a safety rupture disc. Further, a slurry containing 50 mg of montmorillonite obtained in the below-mentioned (3) and 15 mmol (calculated as Al atom) of triisobutyl aluminum were charged into the catalyst feeder. Thereafter, 700 ml of propylene was charged into the autoclave. The safety rupture disc of the catalyst feeder was broken at room temperature, and the contents of the autoclave were heated to 80° C., and propylene was polymerized for 35 minutes, thereby obtaining 163 g of polypropylene. As a result of the measurements, it was confirmed that the catalyst activity was 3260 and the complex activity was $25.0 \times 10^4$. Further, it was confirmed that the obtained polypropylene had a melting point (Tm) of 152.7° C., a melt flow rate (MFR) of 0.8, a weight-average molecular weight (Mw) of $4.1 \times 10^5$ and a ratio Q (Mw/Mn) of 2.6.

(3) Chemical Treatment of Clay Minerals and Preparation of Solid Catalyst Component:

10 g of montmorillonite ("KUNIPIA F" produced by Kunimine Kogyo Co., Ltd.) was dispersed in dilute sulfuric acid comprising 10 g of sulfuric acid and 90 ml of desalted water, and the obtained mixture was heated to a boiling point thereof, and then stirred for 6 hours. Thereafter, the recovered montmorillonite was sufficiently washed with desalted water, and after pre-drying, dried at 200° C. for 2 hours, thereby obtaining chemically-treated clay minerals. 200 mg of the thus chemically-treated montmorillonite was mixed with 0.8 ml of a toluene solution containing triethyl aluminum in an amount of 0.5 mol/liter, and the mixture was stirred at room temperature for one hour. Thereafter, the mixture was washed with toluene, thereby obtaining a montmorillonite-toluene slurry having a concentration of 33 mg/ml.

EXAMPLE 14

4 mmol (calculated as Al atom) of methyl alumoxane ("MMAO" produced by Toso-Akzo Co., Ltd.) and 0.298 mg of the racemic compound obtained in Example 13(1) were charged into a 2-liter stirring-type autoclave. Further, 1,500 ml of propylene was charged into the autoclave and the content of the autoclave was heated to 70° C. to conduct the polymerization of propylene for one hour, thereby obtaining 32 g of polypropylene. As a result of the measurements, it was confirmed that the complex activity was $10.7 \times 10^4$, and the obtained polypropylene had a melting point (Tm) of 154.4° C., a melt flow rate (MFR) of 0.08, a weight-average molecular weight (Mw) of $8.4 \times 10^5$ and a ratio Q (Mw/Mn) of 3.8.

EXAMPLE 15

(1) Chemical Treatment of Clay Minerals:

22.20 g of commercially available montmorillonite ("KUNIPIA F" produced by Kunimine Kogyo Co., Ltd.) was dispersed in a solution prepared by dissolving 15.96 g of $MgSO_4$ in 134 ml of desalted water. The obtained dispersion was stirred at 86° C. for one hour, thereby obtaining a wet cake. Next, the obtained wet cake was dispersed in a solution prepared by dissolving 23.38 g of sulfuric acid and 29.16 g of $MgSO_4$ in 69.24 ml of desalted water, and the obtained dispersion was refluxed for 2 hours. Thereafter, the obtained cake was filtered out, washed with water until the pH thereof reached 6, and then dried at 100° C. for 3 hours. Then, the obtained dry cake was pulverized in a porcelain mortar and passed through a sieve, thereby separating particles having a particle size of not more than 105 μm therefrom. The obtained particles were dried at 200° C. for 2 hours under reduced pressure, thereby obtaining a component (D).

(2) Production of Solid Catalyst Component and Prepolymerization Treatment:

0.8796 g of the component (D) obtained in the above (1) and then 3.5 ml of a toluene solution containing triethyl aluminum in an amount of 0.50 mmol/ml, were successively introduced into a 100 ml flask in a nitrogen atmosphere, and stirred at room temperature for 45 minutes. Then, a solid was filtered out and washed with toluene until the washing efficiency reached 1/100. Thereafter, the solid was mixed with 15 ml of toluene to form a toluene slurry. Separately, 0.6 ml of a toluene solution containing triisobutyl aluminum in an amount of 0.50 mmol/ml and 19.1 ml of a toluene solution containing the racemic compound produced in Example 13(1) in an amount of 1.5 μmol/ml, were introduced into a 100 ml flask, and stirred at room temperature, thereby obtaining a solution. The obtained solution was introduced into the above toluene slurry, thereby producing a slurry of solid catalyst component. 40 ml of toluene and then 36 ml of the solid catalyst component slurry obtained above were introduced into a 2-liter stirring-type autoclave at room temperature in a nitrogen atmosphere. While maintaining the temperature of the autoclave at 24° C., 104 ml of propylene was charged into the autoclave, and the content of the autoclave was prepolymerized for 3 minutes, thereby obtaining a prepolymerization catalyst slurry. The amount of the polymer produced per 1 g of the solid catalyst component was 2.98 g. The concentration of the solid catalyst component in the obtained prepolymerization catalyst slurry was 12.5 mg/ml.

(3) Block Polymerization of Propylene:

0.40 mmol of triisobutyl aluminum, 50.0 mg of the prepolymerization catalyst (calculated as the solid catalyst component) obtained in the above (2), 200 ml of hydrogen and 1,500 ml of liquid propylene were introduced into a 2-liter stirring-type autoclave. Then, the contents of the autoclave were heated to 75° C., and polymerized for 45 minutes. Thereafter, residual propylene was purged to stop the polymerization reaction, thereby obtaining 289 g of polypropylene. As a result of the measurements, it was confirmed that the catalyst activity was 5780 and the complex activity was $2.4 \times 10^5$. The obtained polypropylene had a melting point (Tm) of 151.8° C. and a melt flow rate (MFR) of 14.2. After 17 g of polypropylene was removed from the autoclave under a nitrogen stream, and while maintaining the autoclave at 60° C., propylene was charged into the autoclave until the inner pressure of the autoclave reached 10 kgf/cm²G. Further, ethylene was introduced into the autoclave until the inner pressure reached 20 kgf/cm²G. An ethylene/propylene mixed gas having a propylene partial pressure of 49.97% was appropriately introduced into the autoclave, and polymerized for 80 minutes while maintaining the inner pressure at 20 kgf/cm²G. Thereafter, a residual ethylene/propylene mixed gas was purged to stop the polymerization reaction, thereby obtaining 46 g of an ethylene/propylene rubber component. As a result of the measurements, it was confirmed that the catalyst activity was 978 and the complex activity was $4.0 \times 10^4$. The content of a rubber component in the obtained block copolymer was 14.5% by weight, and the melt flow rate (MFR) thereof was 7.0.

Industrial Applicability

Hitherto, in order to obtain a silyl- or germyl-substituted cyclopentadienyl compound constituting a ligand of a metallocene compound used as, for example, a catalyst for the polymerization of α-olefin, it has been required to conduct the production reaction for a long period of time. Further, the yield was unsatisfactory. Especially, in the case where two or more sterically bulky substituent groups are bonded to a silicon atom or a germanium atom, the above disadvantageous tendency becomes more remarkable and the yield is further deteriorated. On the other hand, in accordance with the present invention, for example, the silyl- or germyl-substituted cyclopentadienyl compound can be produced for a short time with a high yield.

What is claimed is:

1. A process for producing a silicon- or germanium-containing organic compound (iv), comprising:
   reacting an alkali metal- or alkali earth metal-containing organic compound (i) with a leaving group- and silicon- or germanium-containing compound (ii) in the presence of a nitrogen-containing aromatic heterocyclic compound (iii).

2. A process according to claim 1, wherein said compound (i) is represented by the general formula (I), (II) or (III):

$A\text{-}M^1$ (I)

$A\text{-}M^2\text{-}A$ (II)

$A\text{-}M^2\text{-}X$ (III)

wherein $M^1$ is an alkali metal; $M^2$ is an alkali earth metal; A is a cyclopentadienyl group which may have a condensed ring thereon, an alkyl group, an aryl group, an allyl group, a vinyl group or a heterocyclic group; X is a halogen atom; the above groups may have substituent(s); and the two As in the general formula (II) may be different from each other.

3. A process according to claim 2, wherein said compound (i) has at least one cyclopentadienyl group.

4. A process according to claim 2, wherein said compound (i) has at least one cyclopentadienyl group having a condensed ring.

5. A process according to claim 2, wherein said compound (i) is an alkali metal salt or an alkali earth metal salt of a cyclopentadienyl compound represented by the following general formula (IV):

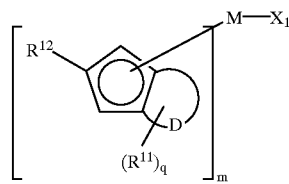

(IV)

wherein $R^{11}$ is a $C_1$ to $C_{20}$ hydrocarbon group or $C_1$ to $C_{20}$ hydrocarbon group containing a nitrogen, oxygen, sulfur, silicon or halogen; $R^{12}$ is a hydrogen atom, a $C_1$ to $C_{10}$ hydrocarbon group or $C_1$ to $C_{10}$ hydrocarbon group containing a nitrogen, oxygen, sulfur or halogen, a $C_1$ to $C_{18}$ hydrocarbon group containing silicon or a halogen atom; D is a saturated or unsaturated $C_3$ to $C_8$ divalent hydrocarbon group; M is an alkali metal or an alkali earth metal; q is an integer of 0 to 16; m is an integer of 1 or 2; 1 is an integer of 0 or 1; and when m is 2, 1 is 0.

6. A process according to claim 1, wherein said compound (ii) is represented by the following general formula (V):

(V)

wherein Q is a silicon atom or a germanium atom; B is a halogen atom, a substituted or unsubstituted alkylsulfonyloxy group or a substituted or unsubstituted arylsulfonyloxy group; $R^1$ and $R^2$ are a substituted or unsubstituted hydrocarbon group or a substituted or unsubstituted cyclic hydrocarbon group formed together with Q to which $R^1$ and $R^2$ are bonded; and n is an integer of 0 to 3.

7. A process according to claim 1, wherein said compound (ii) is a halogenated silicon compound or a halogenated germanium compound.

8. A process according to claim 1, wherein said compound (iii) is a nitrogen-containing aromatic heterocyclic compound which has 1 to 6 nitrogen atoms, and may have a condensed ring and/or a substituent.

9. A process according to claim 7, wherein said nitrogen-containing aromatic heterocyclic compound is selected from the group consisting of pyrroles, pyrazoles, imidazoles, triazoles, tetrazoles, pyridines, pyridazines, indolizines, pyrimidines, pyrazines, symmetric triazines, asymmetric triazines, thiazoles, isothiazoles, oxazoles, isoxazoles, indoles, isoindoles, 1H-indazoles, purines, benzo[d]isoxazoles, benzo[d]isothiazoles, benzo[d]imidazoles, benzo[d]oxazoles, benzo[d]thiazoles, quinolines, isoquinolines, cinnolines, phthalazines, naphthyridines, quinoxalines, quinazolines, pteridines, carbazoles, β-carbolines, phenanthridines, acridines, perimidines, phenanthrolines, phenazines and phenarsazines.

10. A process according to claim 1, wherein said compound (i) is an alkali metal salt or an alkali earth metal salt of a cyclopentadienyl compound, and said compound (ii) is a silicon compound or a germanium compound which is substituted with a halogen atom, a substituted or unsubstituted alkylsulfonyloxy group or a substituted or unsubstituted arylsulfonyloxy group.

* * * * *